(12) United States Patent
Brunner et al.

(10) Patent No.: US 12,611,146 B2
(45) Date of Patent: Apr. 28, 2026

(54) SYSTEMS AND METHODS TO REMOVE BRAIN STIMULATION ARTIFACTS IN NEURAL SIGNALS

(71) Applicant: Washington University, St. Louis, MO (US)

(72) Inventors: Peter Brunner, St. Louis, MO (US); Tao Xie, St. Louis, MO (US); Jon Willie, St. Louis, MO (US); Eric Leuthardt, St. Louis, MO (US)

(73) Assignee: WASHINGTON UNIVERSITY, St. Louis, MO (US)

( * ) Notice: Subject to any disclaimer, the term of this patent is extended or adjusted under 35 U.S.C. 154(b) by 478 days.

(21) Appl. No.: 18/163,257

(22) Filed: Feb. 1, 2023

(65) Prior Publication Data

US 2023/0240618 A1 Aug. 3, 2023

Related U.S. Application Data

(60) Provisional application No. 63/305,593, filed on Feb. 1, 2022.

(51) Int. Cl.
*A61B 5/00* (2006.01)
*A61B 5/372* (2021.01)
*G16H 40/67* (2018.01)

(52) U.S. Cl.
CPC ............ *A61B 5/7217* (2013.01); *A61B 5/372* (2021.01); *G16H 40/67* (2018.01)

(58) Field of Classification Search
CPC ...... A61B 5/7217; A61B 5/372; G16H 40/67; G16H 40/63; G16H 50/50
See application file for complete search history.

(56) References Cited

U.S. PATENT DOCUMENTS

| | | | | |
|---|---|---|---|---|
| 9,351,688 B2 * | 5/2016 | Iyer | .................... | A61B 5/14552 |
| 9,414,758 B1 * | 8/2016 | Brockway | ............ | A61B 5/6804 |
| 2005/0144042 A1 * | 6/2005 | Joffe | ...................... | G16H 10/60 |
| | | | | 705/2 |
| 2014/0018693 A1 * | 1/2014 | Hou | ........................ | A61B 5/369 |
| | | | | 600/544 |

(Continued)

OTHER PUBLICATIONS

Chandran et a., Comparison of Matching Pursuit Algorithm with Other Signal Processing Techniques for Computation of the Time-Frequency Power Spectrum of Brain Signals, Journal of Neuroscience, 2016, 36 (12), pp. 3399-3408.

*Primary Examiner* — Jeffrey G. Hoekstra

(57) ABSTRACT

Computing systems and computer-implemented methods for removing brain stimulation artifacts in neural signals are disclosed. The method makes use of a matching pursuit algorithm to accurately extract the stimulation artifact. The disclosed method removes the stimulation artifact associated with individual stimulation pulses without needing additional information from previous stimulation pulses or other electrodes. The disclosed method is compatible for use with various stimulation frequencies, does not need any filtering, and can recover neural signals almost immediately after stimulation. The disclosed method is compatible for use in has great potential in closed-loop systems used in various neurological diagnostic and therapeutic procedures.

10 Claims, 32 Drawing Sheets
(20 of 32 Drawing Sheet(s) Filed in Color)

(56)    References Cited

U.S. PATENT DOCUMENTS

| 2015/0080671 | A1* | 3/2015 | Christensen | A61B 5/4082 |
| | | | | 600/301 |
| 2016/0206880 | A1* | 7/2016 | Koubeissi | A61B 5/316 |
| 2016/0242690 | A1* | 8/2016 | Principe | A61B 5/316 |
| 2017/0172493 | A1* | 6/2017 | Rahman | A61B 5/6801 |
| 2017/0340292 | A1* | 11/2017 | Rossi | A61B 5/7253 |
| 2017/0360377 | A1* | 12/2017 | Rossi | A61B 5/7253 |
| 2019/0166434 | A1* | 5/2019 | Petley | H04R 25/505 |
| 2021/0338176 | A1* | 11/2021 | Kahl | G16H 40/63 |
| 2023/0240618 | A1* | 8/2023 | Brunner | G16H 40/63 |
| | | | | 705/2 |

* cited by examiner

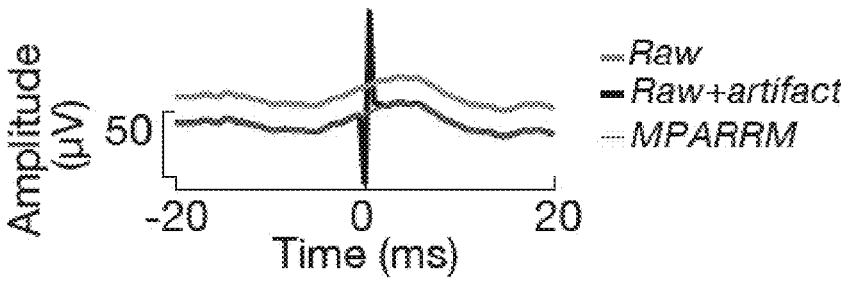
FIG. 9A1
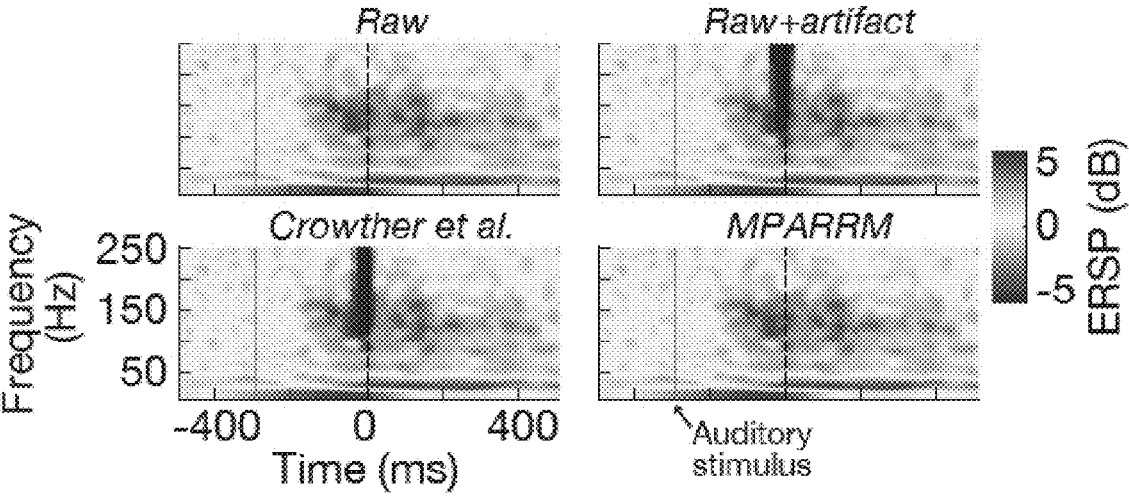
FIG. 9A2
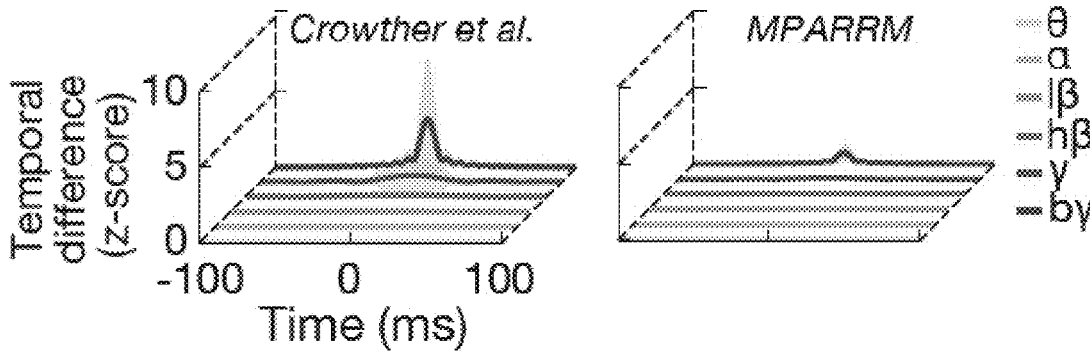
FIG. 9A3

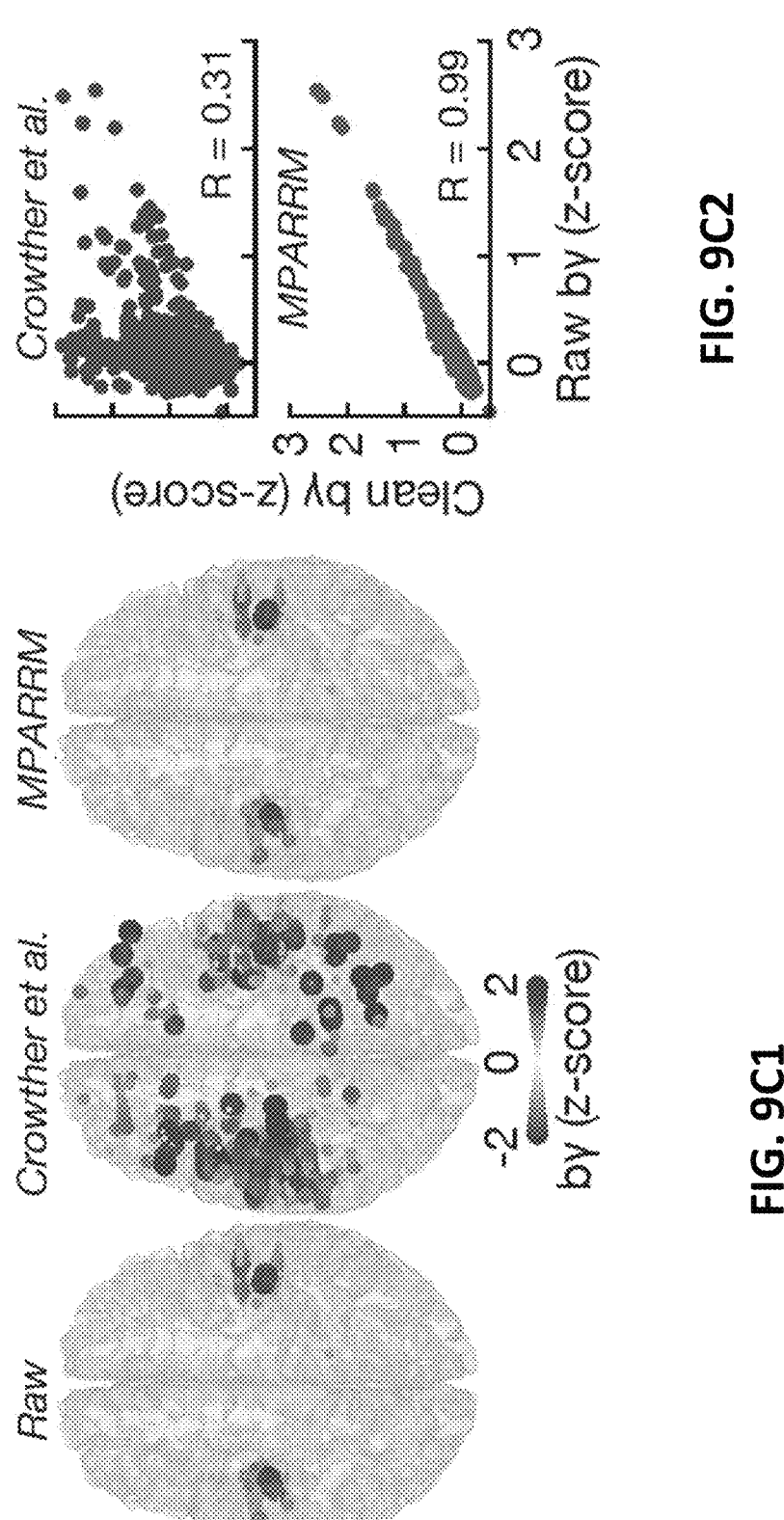
FIG. 9C2
FIG. 9C1

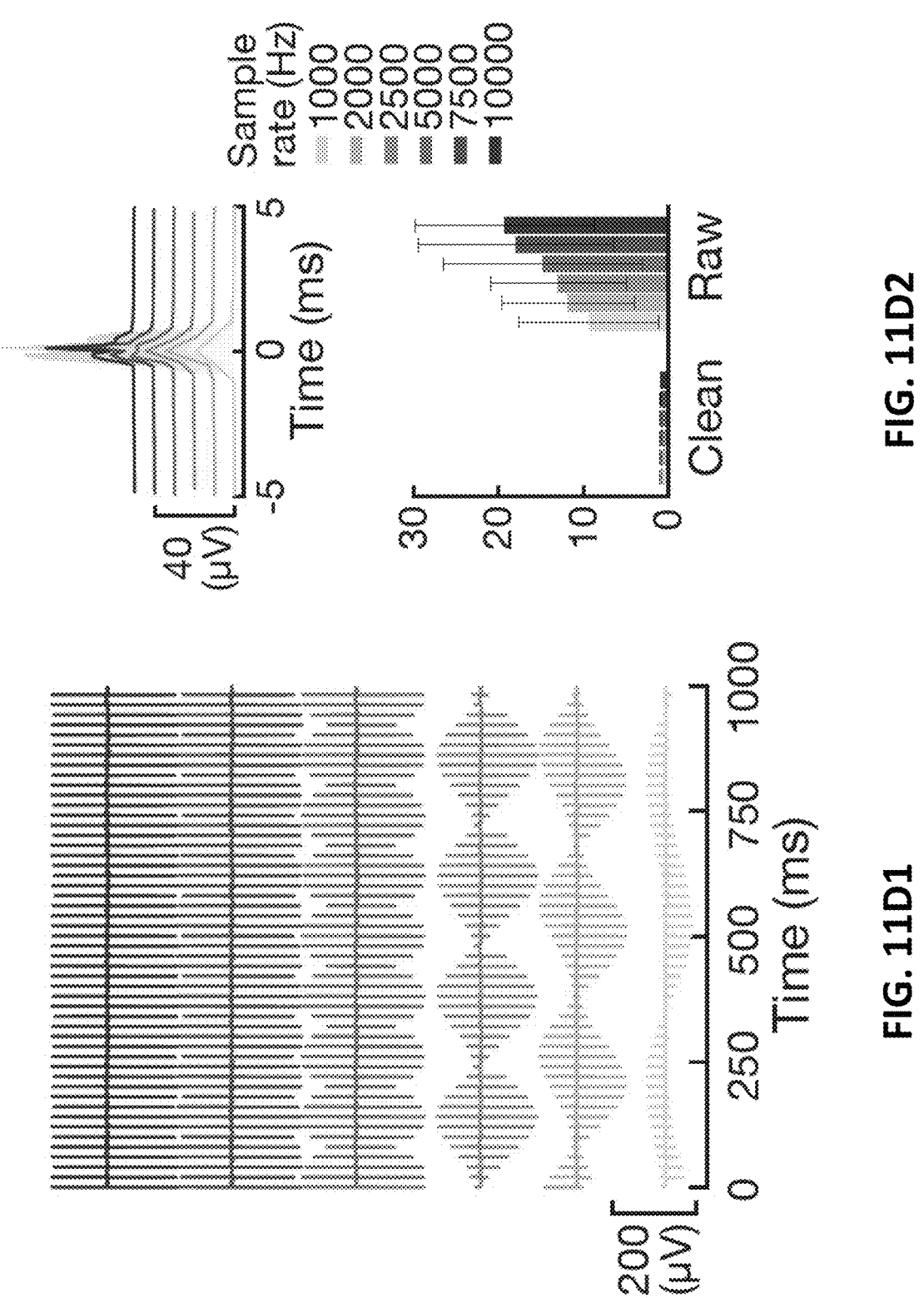
FIG. 11D2
FIG. 11D1

SYSTEMS AND METHODS TO REMOVE BRAIN STIMULATION ARTIFACTS IN NEURAL SIGNALS

CROSS-REFERENCE TO RELATED APPLICATIONS

This application claims the benefit of priority to U.S. Provisional Application No. 63/305,593 filed on Feb. 1, 2022, the content of which is incorporated by reference herein in its entity.

STATEMENT REGARDING FEDERALLY SPONSORED RESEARCH OR DEVELOPMENT

This invention was made with government support under EB018783, NS108916, NS109103, EB026439, MH122258, and MH120194 awarded by the National Institutes of Health. The government has certain rights in the invention.

MATERIAL INCORPORATED-BY-REFERENCE

Not applicable.

FIELD OF THE DISCLOSURE

The present disclosure generally relates to computing systems and computer-implemented methods for removing brain stimulation artifacts in neural signals.

BACKGROUND

Brain stimulation techniques are powerful tools for understanding basic neuroscience questions and various neurological diagnose and therapies. Non-invasive brain stimulation including repetitive transcranial magnetic stimulation (rTMS), single-pulse TMS, transcranial direct current stimulation (tDCS), transcranial random noise stimulation (tRNS), transcranial alternating current stimulation (tACS), transcranial focused ultrasound stimulation (tFUS), vagus nerve stimulation (VNS); invasive brain stimulation including single-pulse electrical stimulation (SEPS), high-frequency stimulation, and micro-stimulation. In these systems, a group of neural targets is stimulated, and the neural response of other brain areas is captured. However, analysis of the neural response is hampered by what is known as stimulation artifacts. The stimulation artifact can be of sufficient magnitude to obscure neural response. Accordingly, the stimulation artifact must be removed if neural responses are effectively measured and used for research and clinical applications. Generally, there are three types of methods to remove the stimulation artifact.

The filtering method removes the stimulation artifacts by lowpass filtering the signal. This method is only suitable for high-frequency stimulation, in which the artifact frequency is far higher than the neural oscillations. However, stimulation with lower frequencies, e.g., frequency in the alpha/beta/gamma range, has also shown efficacy for the modulation of neural activities; neural activity in a high-frequency range is also very important, e.g., broadband gamma within 70-170 Hz is thought to represent the assemble neural firing.

The interpolation method can remove the stimulation artifact by either disconnecting the amplifier circuits during and immediately after the stimulation or using interpolation to replace the artifact time window. However, this method will lose the immediate brain response to the stimulation and it will introduce a sharp artifact at the truncation point.

The template subtraction method can remove the stimulation artifact by subtracting a specific waveform template model. This method assumes that the artifact waveform is regular, or that the template model parameter is constant over time. However, both assumptions cannot meet the actual neuronal activity. And since the template can only be obtained in a posthoc analysis, this method may not be suitable for closed-loop brain stimulation.

The neural responses to single-pulse electrical stimulation (SPES) can provide evidence for direct and indirect structural and functional connectivity. These responses include cortico-cortical evoked potentials (CCEPs) consisting of phase-locked responses revealed by averaging signals in the time domain, and cortico-cortical spectral responses (CCSRs) obtained by averaging activity in the frequency domain that is usually dominated by non-phase-locked responses at high frequencies.

SPES typically consists of a constant-current square-wave pulse (width of 0.1-1 ms) at a fixed frequency of 1 Hz (or 0.2, 0.5, or 2 Hz), and produces large electrical artifacts both immediately at the time of stimulation and afterward. These artifacts typically have a sharp morphology and broad frequency power akin to the Dirac function, followed by a slower capacitive discharge, and may masquerade as a physiological response to electrical stimulation. The CCEPs and CCSRs studies generally exclude 5-20 ms of the signal after stimulation to avoid contamination of the analyses by artifact components, and thus these early responses are simply ignored and missed. However, early responses within 10 ms may reflect mono- or oligosynaptic connectivity, as opposed to more delayed responses which may reflect poly-synaptic connectivity. Thus, there is an urgent need to develop an effective denoising methodology that removes the stimulation artifact, permitting an analysis of the physiological components of the early responses.

Existing stimulation artifact removal methods generally fall into one of three categories: interpolation, template subtraction, and model decomposition. Interpolation over the artifact window is a simple and often effective approach, which can be done with linear interpolation, curve fitting, or linear merging with surrounding signals. However, interpolation techniques are useful only for investigative questions that can ignore the CCSRs and other activities around the window of stimulation, as the spectral power of the artifact will spread in time due to filtering. Template subtraction techniques are typically performed by computing an average temporal- and amplitude-optimized template from individual trials, and subtracting this from each stimulus artifact window. There are several versions of this technique, some of which have been extended by using machine learning, biophysical models, or dictionary learning. However, these template subtraction methods generally assume that consecutive artifacts of stimulation pulses are similar or congruent in shape. However, the neural signals are usually recorded at a much lower sampling rate (e.g., 1 kHz) compared with the hardware digitized sampling rate (e.g., 50 kHz). As a consequence, The individual stimulation artifact shape is no longer identically represented by the digitized samples but varies substantially with the relative phase of the sampling time points, and with different sampling rates. Finally, model decomposition techniques use information from multiple, simultaneously-recorded channels to estimate signals during the stimulation window. Several model techniques have been described, including independent component analysis, principal component analysis, and Gaussian processes. However, model decomposition techniques require large datasets to obtain estimates, significantly hampering their use. In addition, while previously published stimulation artifact removal techniques have been used with variable success to distinguish CCEPs, there is limited evidence of their validity on early (e.g., <20 ms) signal power changes, limiting their utility in CCSR analysis.

Accordingly, there remains a need for novel unsupervised methods of accurately estimating and removing stimulation artifacts.

SUMMARY

Among the various aspects of the present disclosure is the provision of systems and methods for removing brain stimulation artifacts in neural signals.

In one aspect, a computer-implemented method of removing brain stimulation artifacts in electrophysiological signals is disclosed that includes decomposing by matching pursuit, using a computing device, a raw signal trace into a plurality of line noise atoms representative of line noise, the raw signal trace comprising a time history of the electrophysiological signals as measured; subtracting, using the computing device, a summation of the plurality of line noise atoms from the raw signal trace to produce a de-noised trace; identifying, using the computing device, a stimulation time window containing a portion of the denoised trace containing a brain stimulation event and replacing a portion of the denoised trace within the stimulation window with a line connecting pre-stimulation window and post-stimulation window portions of the denoised trace to produce a stimulation-free trace; decomposing by matching pursuit, using the computing device, the stimulation-free trace into a plurality of evoked potential atoms representative of evoked potential; subtracting, using the computing device, a summation of the plurality of evoked potential atoms from the de-noised trace to produce an evoked potential-free trace; decomposing by matching pursuit, using the computing device, the evoked potential-free trace into a plurality of stimulation artifact atoms representative of a stimulation artifact; and subtracting, using the computing device, a summation of the plurality of stimulation artifact atoms from the evoked potential-free trace to produce an artifact-free trace. In some aspects, the plurality of line noise atoms, the plurality of evoked potential atoms, and the plurality of stimulation artifact atoms are selected from a stored library of atoms. In some aspects, the stored library comprises a plurality of atoms comprising Gabor atoms, Dirac atoms, sharp Gaussian atoms, and Fourier atoms. In some aspects, the line noise atoms comprise atoms characterized by atom frequencies greater than 55 Hz that extend over the full duration of the raw signal trace. In some aspects, the evoked potential atoms comprise atoms characterized by atom frequencies less than 70 Hz that extend over a full duration of the raw signal trace. In some aspects, the stimulation artifact atoms comprise atoms characterized by atom frequencies greater than 70 Hz or Dirac atoms that are centered around an onset of the brain stimulation event and extend over less than the full extent of the raw signal trace. In some aspects, the stimulation time window extends from about 5 ms prior to the brain stimulation event to about 5 ms after the brain stimulation event. In some aspects, the method further includes receiving, at the computing device, the raw signal trace. In some aspects, the method further includes isolating a portion of the raw signal trace, the portion comprising signals within a biologically relevant frequency band selected from theta comprising from 4 to 7 Hz, alpha comprising from 8 to 12 Hz, low beta comprising from 13 to 20 Hz, high beta comprising from 20-30 Hz, low gamma comprising from 30-50 Hz, broadband gamma from 70-170 Hz, and any combination thereof. In some aspects, the brain stimulation event comprises a single pulse electrical signal.

Other objects and features will be in part apparent and in part pointed out hereinafter.

DESCRIPTION OF THE DRAWINGS

The patent or application file contains at least one drawing executed in color. Copies of this patent or patent application publication with color drawing(s) will be provided by the Office upon request and payment of the necessary fee.

FIG. 9A1 is a graph summarizing one representative trial of raw human SEEG signal (grey), raw signal added with saline stimulation artifact (black), and clean signal after applying the MPARRM denoising method.

FIG. 9A2 contains maps of representative event-related spectral perturbations (ERSP, EEGLAB) induced by an auditory stimulus. Including raw signal, raw signal add with saline stimulation artifact (time 0), the clean signal after applying the MPARRM denoising method, and the clean signal after applying interpolate denoising method (Crowther et al., 2019).

FIG. 9A3 contains graphs summarizing temporal differences between the raw signals and clean signals within various frequency bands using MPARRM (right) and interpolate denoising method (left).

FIG. 9C1 contains a topographic distribution of auditory-related broadband gamma (by) response for raw signal (left), clean signal using MPARRM denoising method (middle), and clean signal using interpolate denoising methods (right) during the early response window (5 ms to 10 ms following saline stimulation onset).

FIG. 9C2 contains graphs showing the correlation between the by response of raw signal and clean signal using MPARRM (lower, red) and interpolate (upper, blue) denoising methods. Each dot indicates the averaged by during the early response window (5 ms to 10 ms following saline stimulation onset) of each electrode.

FIG. 11D1 contains a representative saline recording with sampling rates ranging from 1000 Hz to 10000 Hz obtained using the scheme illustrated in FIG. 11A.

FIG. 11D2 contains graphs showing recordings (left) from a single trial of the saline SPES artifacts with different sampling rates shown summarized in FIG. 11D1, and summarizing the performance (bottom) of the MPARRM on removing the saline SPES artifacts. The shape of the artifact varied with sampling rate. For each pulse shape, the signal fluctuation (standard deviation) was calculated during the baseline window (1000 ms to 200 ms preceding the stimulation onset) and artifact window (1 ms preceding and 1 ms following stimulation onset) signals, separately using signals from all trials, and the signal fluctuation ratio between the artifact window and baseline window was then calculated. An expected ratio value (bottom) equal to ~1 if the artifact has been successfully removed. For the raw signals, the averaged (mean±s.d., n=110) ratio of all pulse shapes was 9.4±8.2, 11.9±7.9, 13.0±8.0, 14.8±11.8, 18.0±11.5, 19.3±10.6 for different sampling rates. For the clean signals, the averaged (mean±s.d., n=110) ratio of all pulse shapes was 0.91±0.09, 0.92±0.09, 0.93±0.08, 0.92±0.08, 0.95±0.08 0.92±0.06. The results demonstrated that MPARRM could remove the artifact for different pulse shapes and different sampling rates.

FIG. 11E is a table summarizing individual parameter sets used to specify the stimulations used in the experiment summarized in FIG. 11A.

Figure 1:
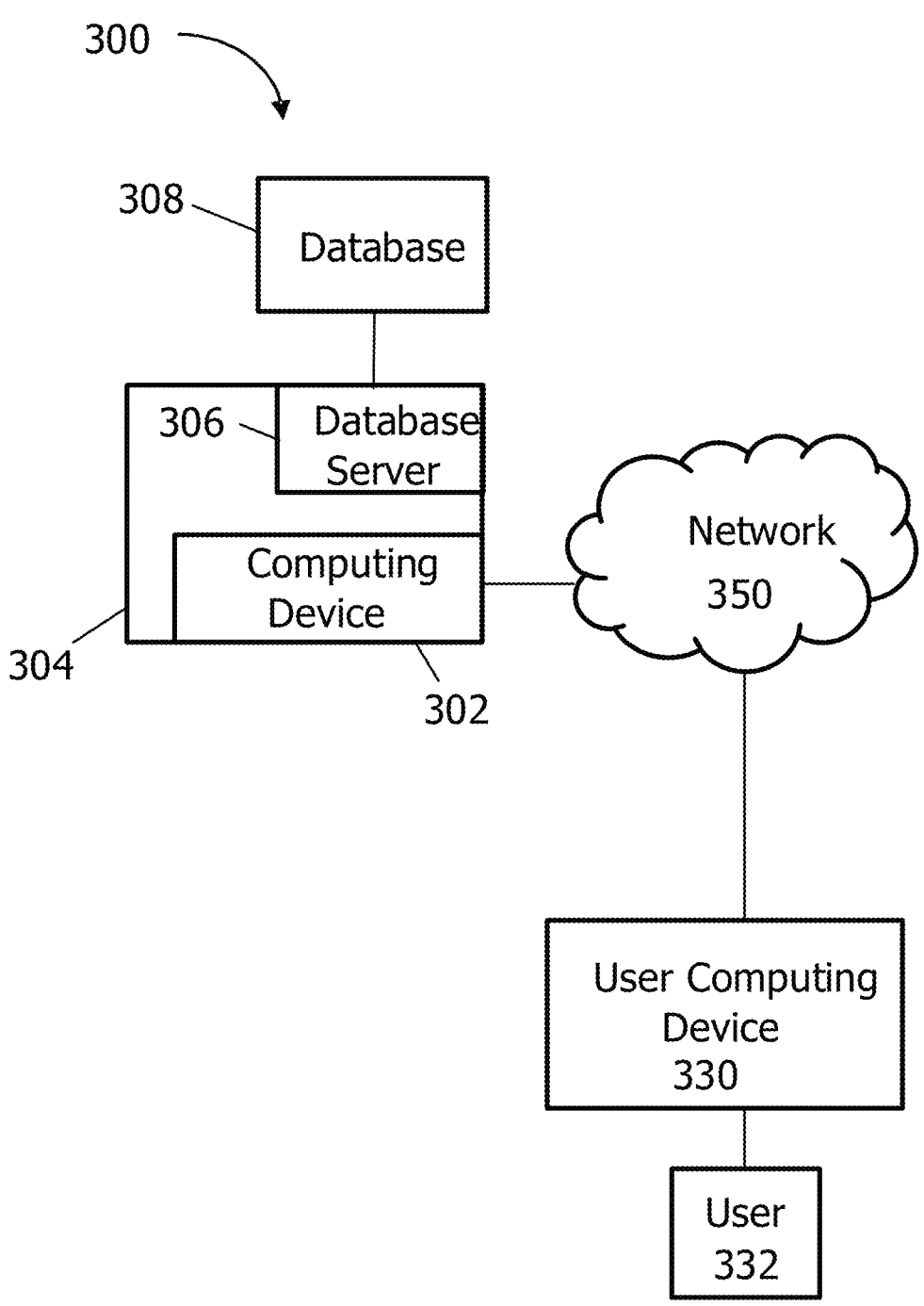
FIG. 1 is a block diagram schematically illustrating a system in accordance with one aspect of the disclosure.

Those of skill in the art will understand that the drawings, described below, are for illustrative purposes only. The drawings are not intended to limit the scope of the present teachings in any way.

DETAILED DESCRIPTION

In various aspects, a matching pursuit-based artifact reconstruction and removal method (MPARRM) capable of removing artifacts from stimulation artifact-affected electrophysiological signals is disclosed. MPARRM reconstructs the stimulation artifacts based on signal information from each trial based on the shape characteristics of the stimulus artifact. This methodology is built on prior matching pursuit-based techniques (Chandran K S et al., 2016), and is specifically powerful for denoising biologically relevant frequency bands (e.g., theta, alpha, beta, and gamma) signals during the early response period. The disclosed MPARRM facilitates investigations of frequency-specific neural activity before, during, and after stimulation.

The disclosed MPARRM method presents a robust solution for the removal of single-pulse electrical stimulation-related artifacts. It could faithfully remove the stimulation artifact without corrupting the electrophysiologic signal components. Specifically, it allows for extracting the spectral responses in the early period, which would have a great impact on both basic neuroscientific studies and neurological therapies.

We developed a novel matching pursuit-based artifact reconstruction and removal method (MPARRM) to accurately remove the stimulation artifact induced by single-pulse electrical stimulation (SPES). The MPARRM is a type of model decomposition method with three outstanding characteristics. First, it only uses single-trial information from an individual channel, which is a great advantage when only limited electrodes are implanted. Second, it works for variable stimulation parameters (e.g., pulse shapes) and does not need a specific setting for each parameter, which makes it a robust tool for further application. Further, it can recover neural signals almost immediately after stimulation, which provides an opportunity to probe the early response of SPES.

As demonstrated in the Examples below, the disclosed MPARRM method provides an approach to faithfully remove stimulation artifacts without corrupting the electrophysiologic signal components. MPARRM can remove stimulation artifacts without spectral leakage or temporal spread problems. It works for variable stimulation parameters and can recover the early response of SPES in different frequency bands. Specifically, during the early response window (5 to 10 ms following the SPES onset), the broadband gamma power (70-170 Hz) of the clean signal was highly correlated with the raw signal (R=0.98, Pearson), and the broadband gamma of the clean signal could faithfully reveal the auditory modulation in the raw signal with a 94% sensitivity and 99% specificity. The disclosed MPARRM method facilitates the understanding of neural response mechanisms including, but not limited to, responses to single-pulse electrical signals (SPES).

In various aspects, computing systems and computer-implemented methods to remove brain stimulation artifacts from neural signals are disclosed herein. The disclosed systems and methods provide for the precise extraction of brain stimulation artifacts and removal of these artifacts from neural signals, yielding a practical measurement of neural responses to brain stimulation. The disclosed method is based on the observation that matching pursuit algorithm (see generally Mallat et al., IEEE Trans. Signal Process. 41, 3397-3415, 1993; Chandran K S et al., J. Neurosci. 36, 3399-3408, 2016) was capable of accurately extracting stimulation artifacts. The matching pursuit algorithm, as used herein, refers to a method of iteratively decomposing a signal into a linear expansion of waveforms (atoms) selected from a large over-complete dictionary, in which the waveforms are selected to best match the local signal structures.

In various aspects, the disclosed MPARRM method makes use of a matching pursuit (MP) algorithm. The MP algorithm is an iterative decomposition technique that approximates a time-domain signal to a linear combination of waveforms called atoms. MP-based algorithms have been previously used to separate the spikes from oscillatory activities or broadband activity, estimate the gamma duration, detect epileptic activity, and estimate the single-trial evoked brain responses. In various aspects, the disclosed MPARRM method sequentially extracts the line noise, evoked potentials, and stimulation artifacts using the MP algorithm. In various aspects, the disclosed MPARRM method accurately removes stimulation artifacts without affecting the physiological components of the electrophysiological signal.

Figure 9B:
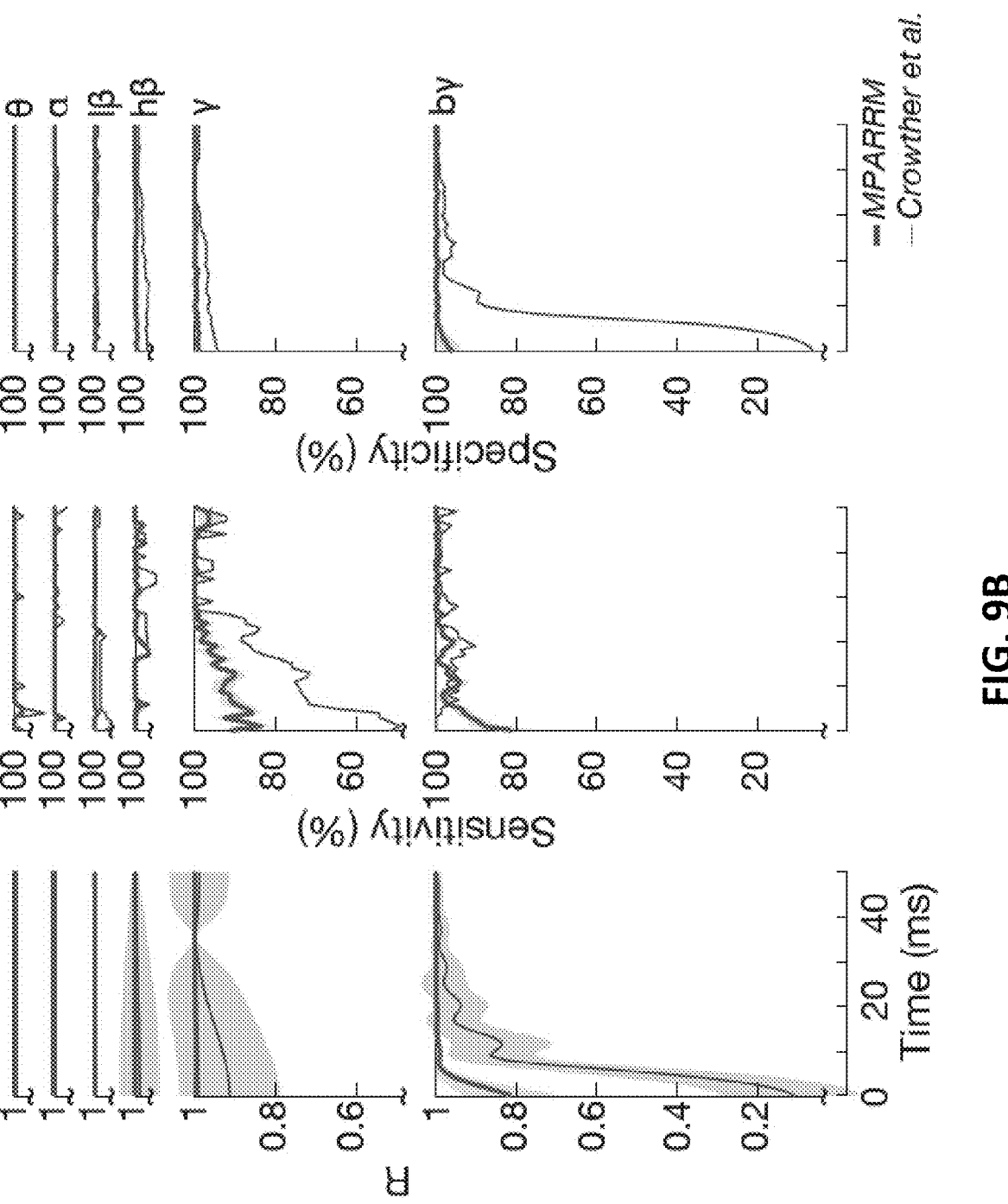
FIG. 9B contains graphs summarizing the correlation between the raw signal and clean signal within various frequency bands using MPARRM (red) and interpolate (blue) denoising methods (left), corresponding sensitivity (middle), and corresponding specificity (right).

By way of non-limiting example, the disclosed MPARRM method is used to remove stimulation artifacts from data obtained during stimulation using single pulse electrical signals (SPES). Without being limited to any particular theory, early electrophysiological responses to SPES could potentially provide vital information. However, the understanding of the spectral responses during the early period is largely unknown, mainly because the stimulation artifact dramatically contaminates the signals nearby due to a filter issue. These spectral responses carry a lot of important information; the power spectral changes of the broadband gamma signals could represent the average firing rate of neurons located directly underneath the recording electrodes. As demonstrated in the Examples herein, the disclosed MPARRM method effectively removes the stimulation artifacts, and the early response of broadband gamma (within 5 ms to 10 ms following stimulation onset) is highly correlated (R=0.98, Pearson correlation) with the ground truth (FIG. 9B).

Figure 11A:
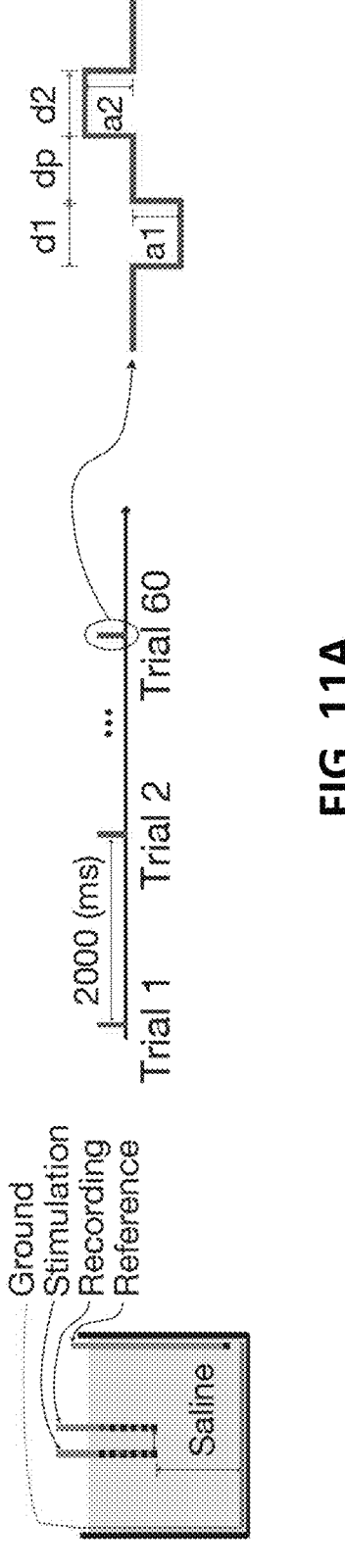
FIG. 11A shows an experimental scheme to generate and record single-pulse electrical stimulation (SPES) artifacts in saline solution. Electrical stimulation pulses were delivered every 2000 ms (one trial), and 60 trials were recorded for each pulse shape. Each stimulation pulse was defined by 5 parameters shown to the far right; d1, dp, and d2 specified the length of each pulse phase, and a1/a2 specified the amplitude of each negative/positive pulse phase, respectively.
Figure 11B:
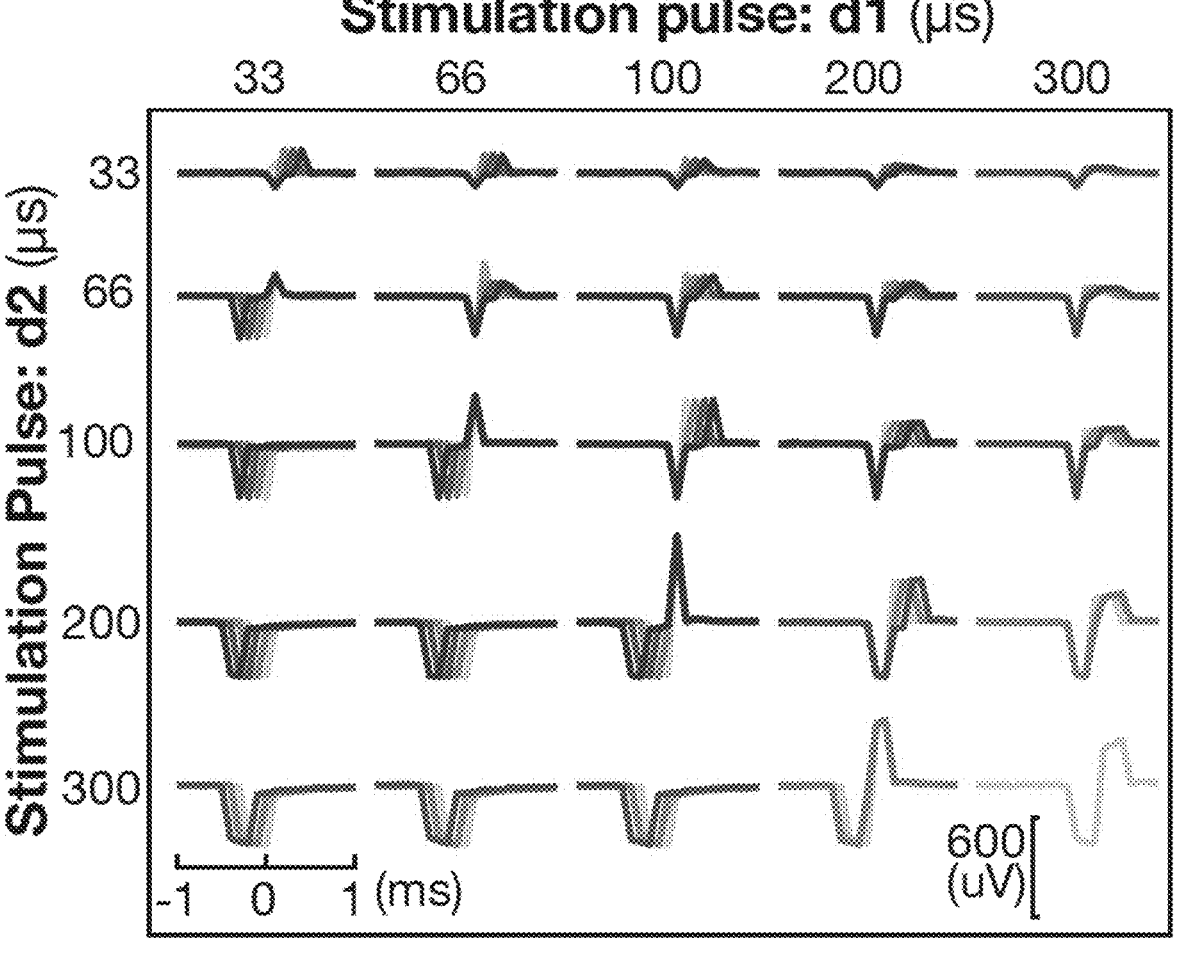
FIG. 11B summarizes 110 different stimulation pulse shapes used in the experiment described in FIG. 11A; pulses were defined using various combinations of d1 (33, 66, 100, 200, 300 μs), d2 (33, 66, 100, 200, 300 μs), dp (0, 66, 100, 200, 300 μs), and a1 (100 μA). The summation of d1, dp, and d2 was limited to no more than 600 μs, and a2 was defined by the function a2=(d1*a1)/d2.
Figure 13:
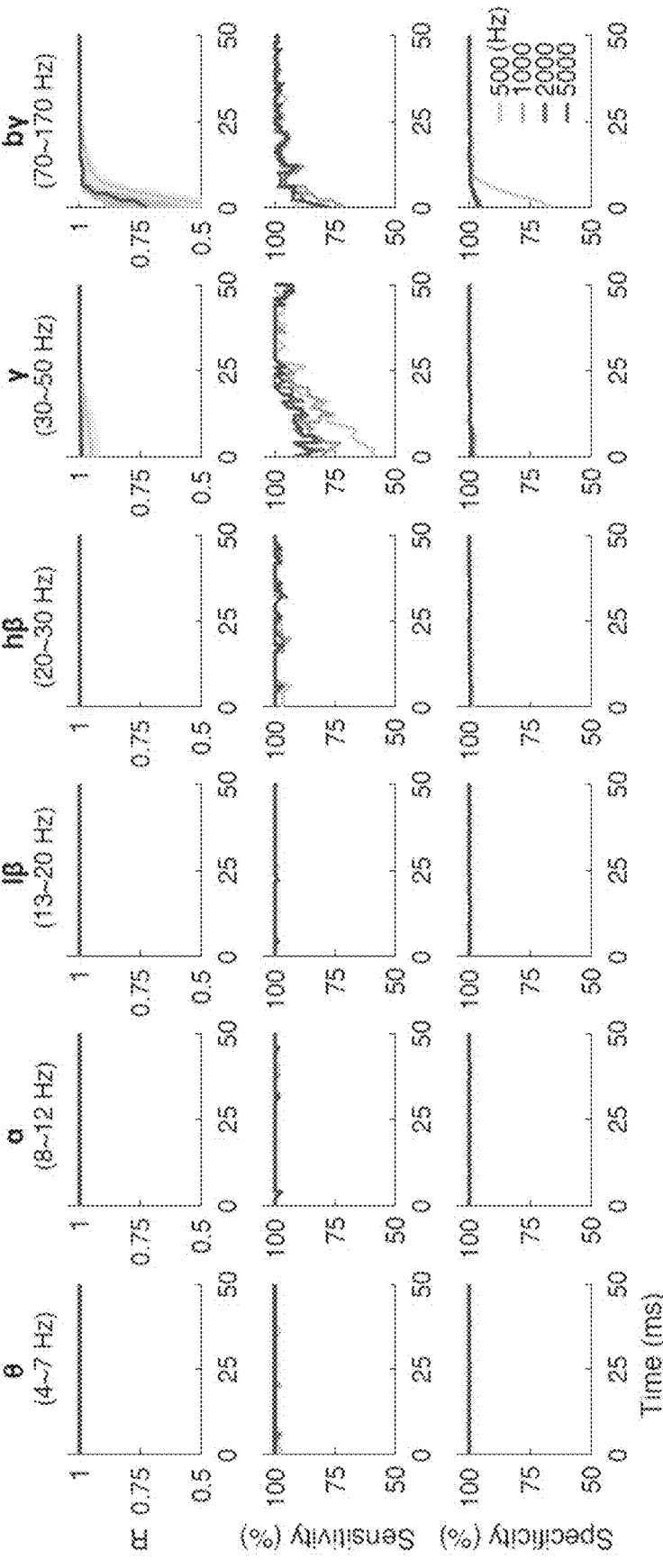
FIG. 13 contains a series of graphs summarizing averaged correlation R (top row), sensitivity (middle row), and specificity (bottom row) for different biologically relevant frequency bands (columns). The averaged correlation R (mean±s.d., n=450, Pearson) between the raw broadband gamma and clean broadband gamma at 5 ms following SPES onset (fifth column) were 0.86±0.08, 0.95±0.03, 0.96±0.03, 0.97±0.02 for sampling rates of 500, 1000, 2000, 5000 Hz, respectively. Similarly, the corresponding sensitivity was 97.2%, 87.5%, 94.4%, 91.6% and the specificity is 91.0%, 99.2%, 98.7%, 98.7% for each sampling rate respectively.
Figure 14A:
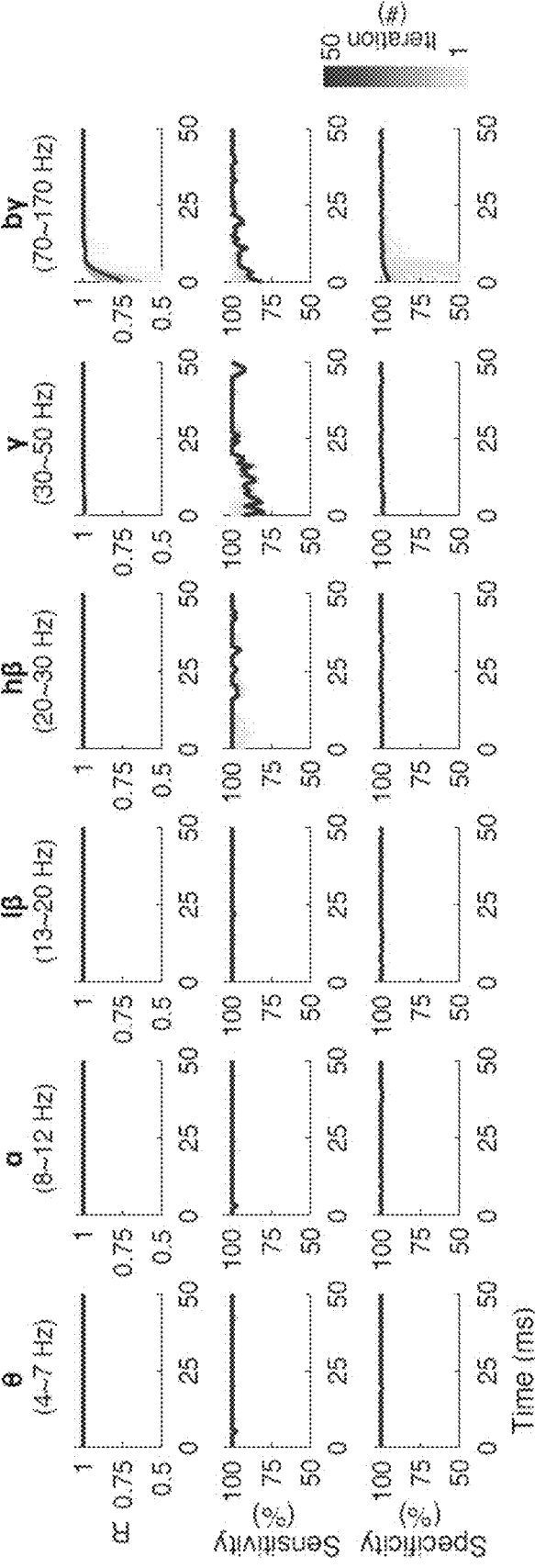
FIG. 14A contains a set of graphs summarizing averaged correlation R (top row), sensitivity (middle row), and specificity (bottom row) for different biologically relevant frequency bands (columns) for different iteration number used during the matching pursuit algorithm.
Figure 14B:
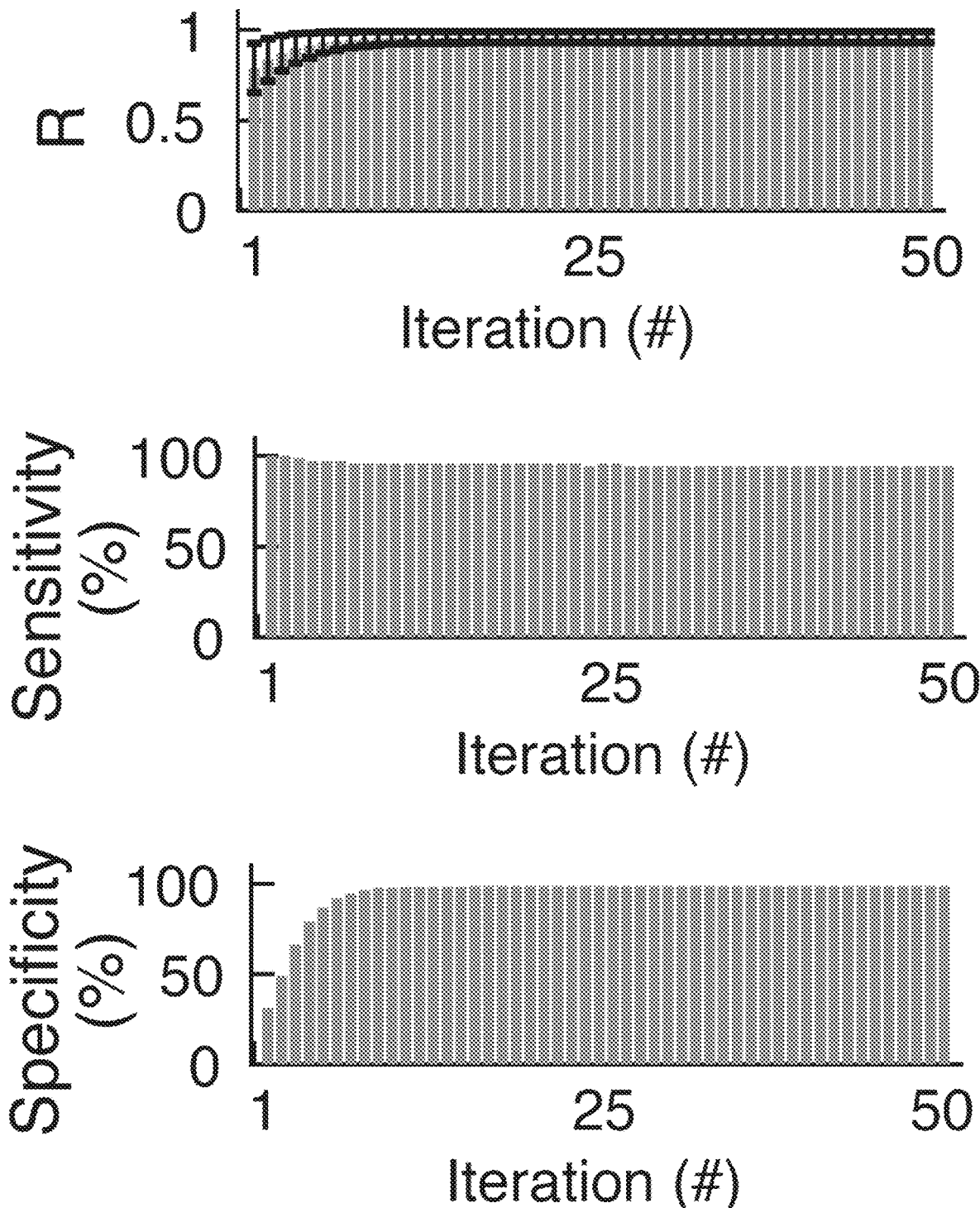
FIG. 14B contains graphs summarizing the effects of the number of iterations on values of averaged correlation R, sensitivity, and specificity obtained from data for broadband gamma at 5 ms after SPES onset shown in FIG. 14A. The performance improved as the iteration number increased. When the iteration number is 10, the averaged correlation R (n=450, Pearson) was 0.95, and the sensitivity and specificity are 95.8% and 97.9%, respectively.

In various aspects, the disclosed MPARRM method removes the artifact from each trial by only involving information of the single-trial signal itself. Consequently, no information from other trials and channels is required. The artifact shapes can vary among different electrodes, times, and even sample rates (FIG. 11B). Because of the greedy fashion of the MP algorithm used by the disclosed MPARRM method, artifacts with different pulse shapes may be removed (FIGS. 11D and 13). In some aspects, the stimulation artifact is assumed to be within a 10 ms window (i.e., 5 ms preceding and 5 ms following stimulation onset). In other aspects, this window length is extended or reduced to any suitable length without limitation to ensure that all stimulation artifacts have been removed.

In various aspects, the number of iterations used to implement the disclosed MPARRM method may be set to any suitable number without limitation. Suitable numbers of iterations may range from about 10 iterations to about 50 or more iterations. Without being limited to any particular theory, reducing the number of iterations results in faster processing of data to remove artifacts using the disclosed MPARRM method.

Figures 5A, 5B:
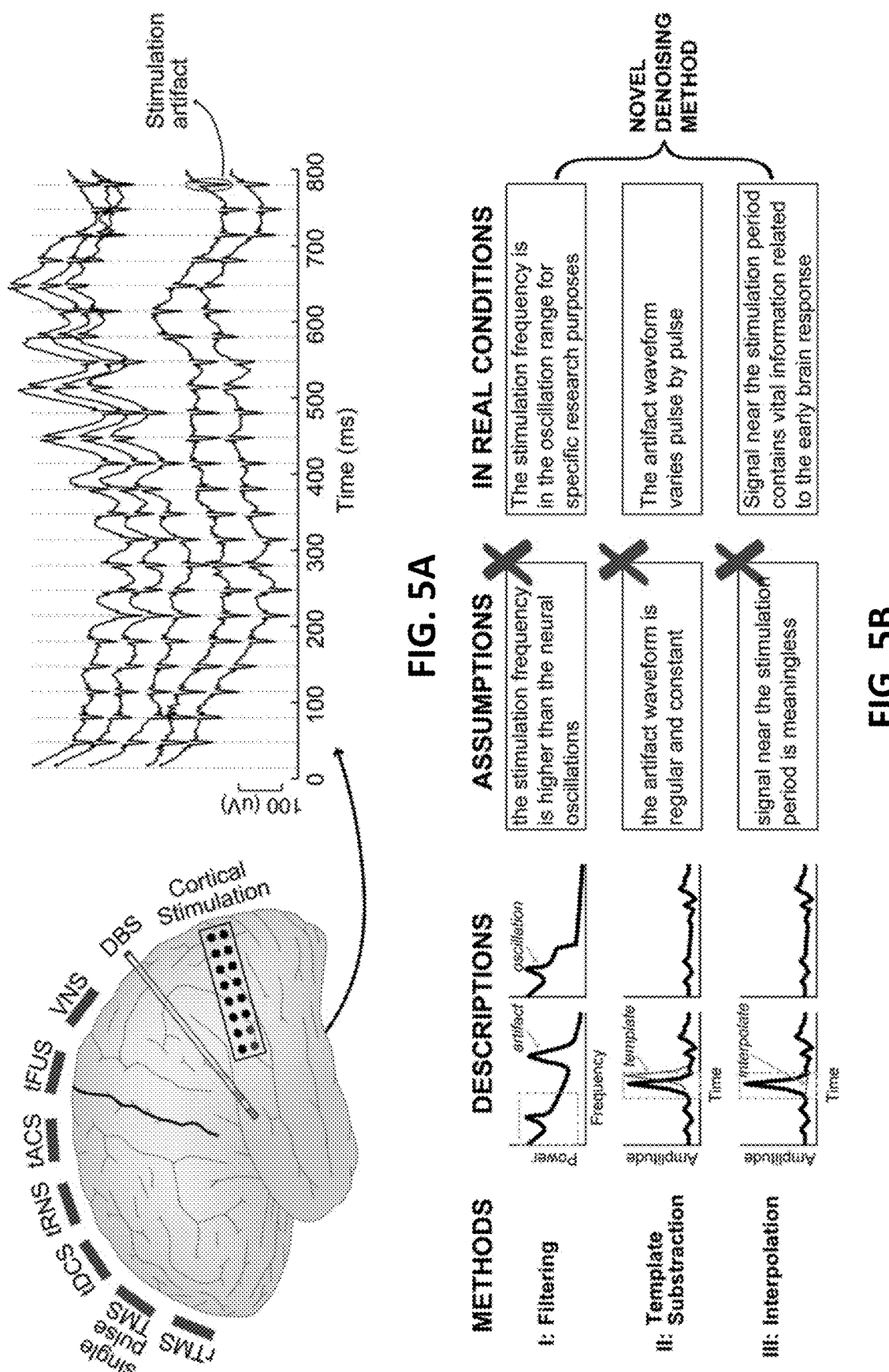
FIG. 5A is a schematic diagram illustrating a process of obtaining neural signals with stimulation artifacts.
FIG. 5B is a schematic diagram illustrating several existing methods of removing stimulation artifacts from neural signals, along with the underlying assumptions of each method.

FIG. 5A is a schematic diagram illustrating an exemplary process of brain stimulation accompanied by the recording of neural signals. The traces shown in the right panel of FIG. 5A are stereo-electroencephalographic signals in the human frontal brain area with 30 Hz vagus nerve stimulation; the dashed lines indicate the onset of individual stimulation pulses. As illustrated in FIG. 1A, brain stimulation techniques typically introduce strong stimulation artifacts around the stimulation period into neural signal traces.

The disclosed method overcomes at least a portion of the limitations of existing artifact extraction methods. FIG. 5B schematically illustrates three existing signal processing techniques to remove stimulation artifacts. However, all these methods are implemented subject to assumptions that are invalid under conditions that typically occur for many brain stimulation methods.

Figure 5C:
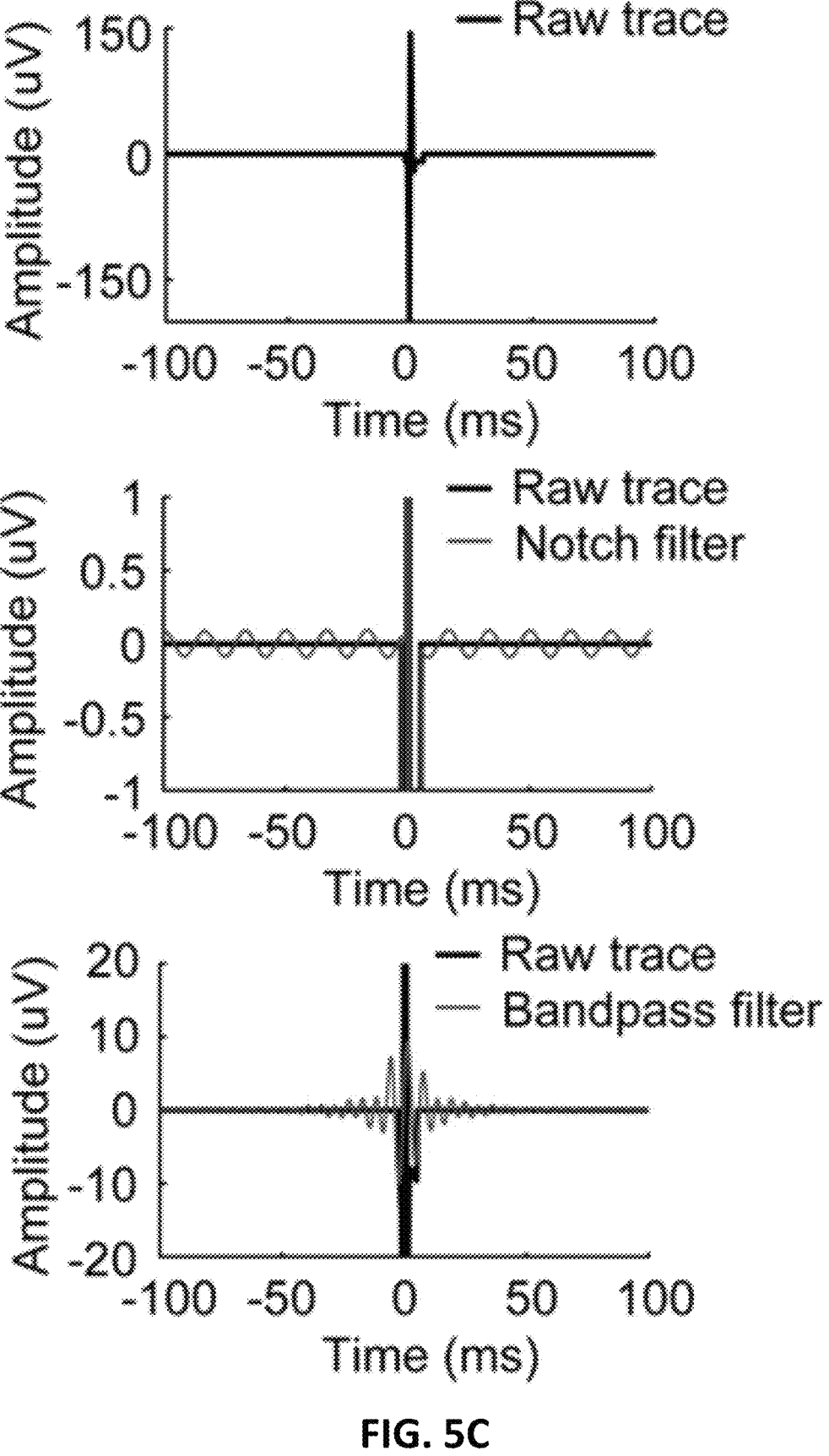
FIG. 5C contains a series of graphs illustrating an existing filtering method for removing stimulation artifacts from a raw signal trace (left) using a notch filter (center) or a bandpass filter (right).

As illustrated in the top row of FIG. 5B, removing stimulation artifacts by filtering via a low-pass filter assumes that the stimulation artifacts occur at a frequency that is higher than naturally occurring neural oscillations. However, in general, stimulation waveforms may be characterized by a variety of frequencies including, but not limited to, frequencies that fall within a frequency range of naturally occurring neural oscillations. FIG. 5C further illustrates the shortcomings of removing stimulation artifacts from neural signal traces by applying one or more filters to the neural trace. As illustrated in FIG. 5C, the stimulation artifact (top graph) is a burst signal with a sharp shape, which will cause spectral leakage around the stimulation period after filtering using a notch filter (middle graph) or bandpass filter (bottom graph). The filters introduce additional artifacts that may be interpreted as fake neural responses, rather than merely removing the stimulation artifacts as intended.

As illustrated in the middle row of FIG. 5B, removing stimulation artifacts by substitution of a template waveform assumes that the stimulation artifact waveforms are regular and constant over repeated stimulation cycles. However, in general, stimulation waveforms may result in artifact waveforms that vary between individual waveforms.

As illustrated in the bottom row of FIG. 5B, removing stimulation artifacts by interpolation of the neural signal trace based on data immediately preceding and following the stimulation artifact essentially discards the neural signal trace obtained during the stimulation cycle and assumes that the neural trace in the immediate vicinity of the stimulation cycle does not contain any useable information.

In various aspects, the disclosed method for removing stimulation artifacts from neural signal traces makes use of the matching pursuit algorithm to decompose the signal trace into a plurality of waveforms selected from a library of atoms/functions, identifying those waveforms within the decomposition that correspond to stimulation artifacts, removing the artifact-associated waveforms, and regenerating a modified neural signal trace using the remaining waveforms, in which the modified neural signal trace includes the raw neural signal trace with the stimulation artifacts removed.

The matching pursuit algorithm (MP) is an iterative procedure to decompose a signal as a linear combination of members of a specified family of functions, referred to herein as "atoms". The matching pursuit algorithm is described in Mallat et al., IEEE Trans. Signal Process. 41, 3397-3415, 1993, the content of which is incorporated by reference herein in its entirety. Briefly, the MP algorithm decomposes any signal into a linear expansion of waveforms that belong to a redundant dictionary, in which each waveform is selected to best match the signal structure. As applied to neural signal traces, the MP algorithm implements an adaptive time-frequency decomposition, in which the neural signal trace is decomposed into a plurality of waveforms selected from a dictionary of time-frequency atoms. The term "atoms", as used herein, refers to dilations, translations, and modulations of single window functions. The MP algorithm is a greedy algorithm that chooses a waveform at each iteration that is best adapted to approximate at least a part of the signal trace. The linear expansion of waveforms is produced over a plurality of iterations, and conservation of energy is invoked to ensure convergence.

In various aspects, the MPARRM method includes subjecting the electrophysiological data to three rounds of matching pursuit to identify line noise, evoked potentials, and stimulation artifacts, respectively. Each round of matching pursuit limits the characteristics of the atoms selected according to separate criteria that represent the expected characteristics of line noise, evoked potential, and stimulation artifact, respectively. Without being limited to any particular theory, the summation of all atoms identified by each round of matching pursuit is thought to correspond to the line noise, evoked potential or stimulation artifact portion of the raw signal, and is subtracted accordingly after each matching pursuit decomposition to produce the data used for the next matching pursuit decomposition.

In various aspects, the atoms associated with line noise are selected if the atom frequency is greater than 55 Hz, and extend along the entire duration of the raw data. In various other aspects, the atoms associated with evoked potential artifacts are selected if the atom frequency is less than 70 Hz. In various additional aspects, the disclosed method makes use of the matching pursuit algorithm to accurately retrieve the stimulation artifact by choosing atoms centered on the stimulation period with specific characteristics. In various aspects, the atoms associated with the stimulation artifact are identified according to at least three selection criteria. In one aspect, an atom is associated with a stimulation artifact if the atom is centered around the stimulation onset time. In another aspect, an atom is associated with a stimulation artifact if the atom frequency is larger than about 70 Hz, or the atom is a Dirac atom. In a third aspect, an atom is associated with a stimulation artifact if the atom is a short atom (i.e. the atom does not extend along the whole time axis).

In various aspects, the MP algorithm selects waveforms from a large over-complete dictionary that includes a plurality of atom types including, but not limited to, Gabor atoms, Dirac atoms, and Fourier atoms. Gabor atoms are sine-modulated Gaussian waveforms that represent a compromise between the frequency and time resolution of a waveform. Dirac atoms are discrete waveforms equal to 1 at one data point and equal to 0 elsewhere and are typically used to extract sharp or abrupt signal waveforms including, but not limited to, stimulation artifacts. Fourier atoms are pure sinusoid signals that are typically used to extract periodic signals including, but not limited to, line noise.

Figure 6A:
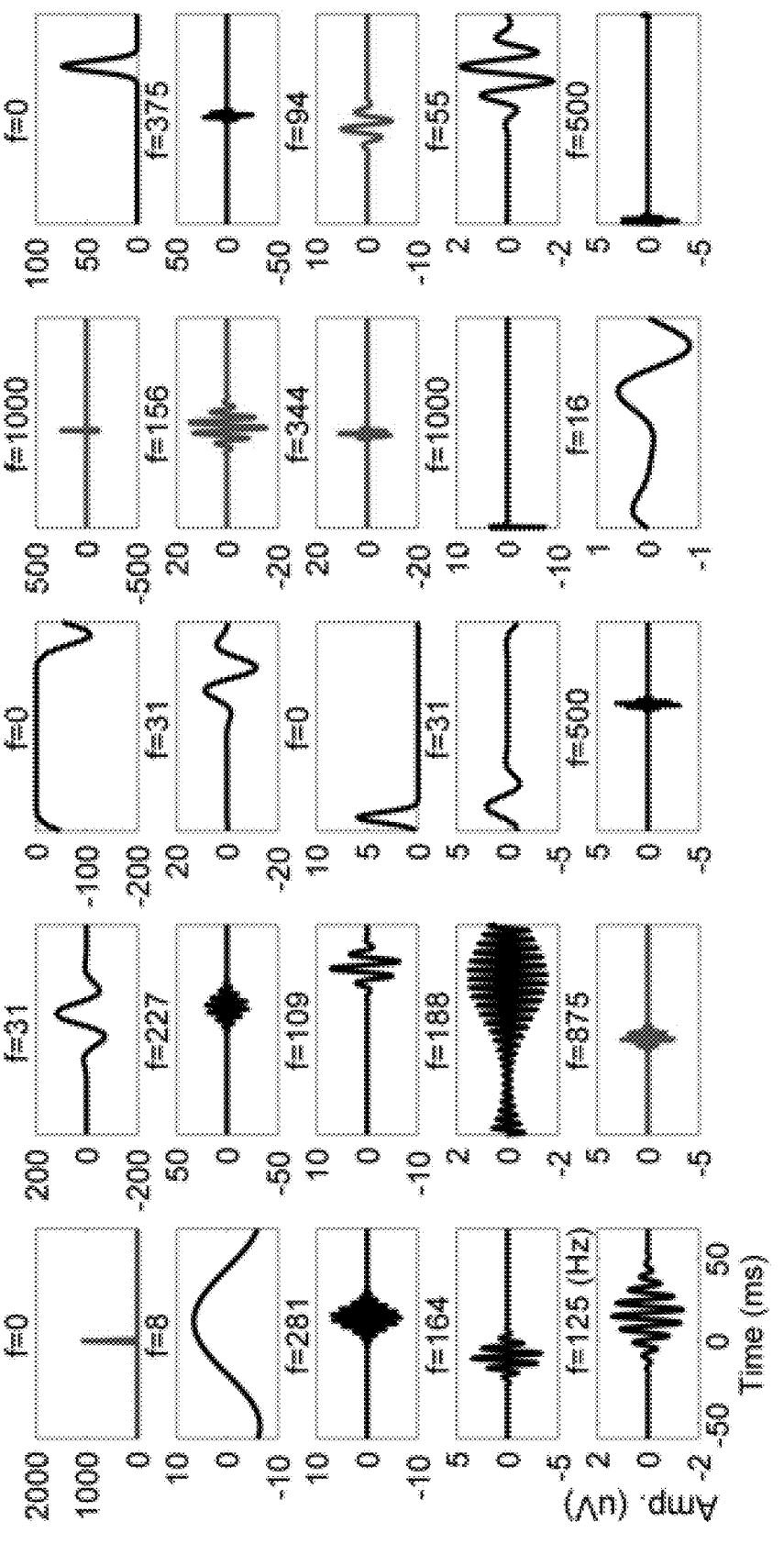
FIG. 6A contains a series of graphs illustrating a plurality of exemplary atoms or functions selected by a matching pursuit method to decompose a neural signal as disclosed herein.
Figure 6A:
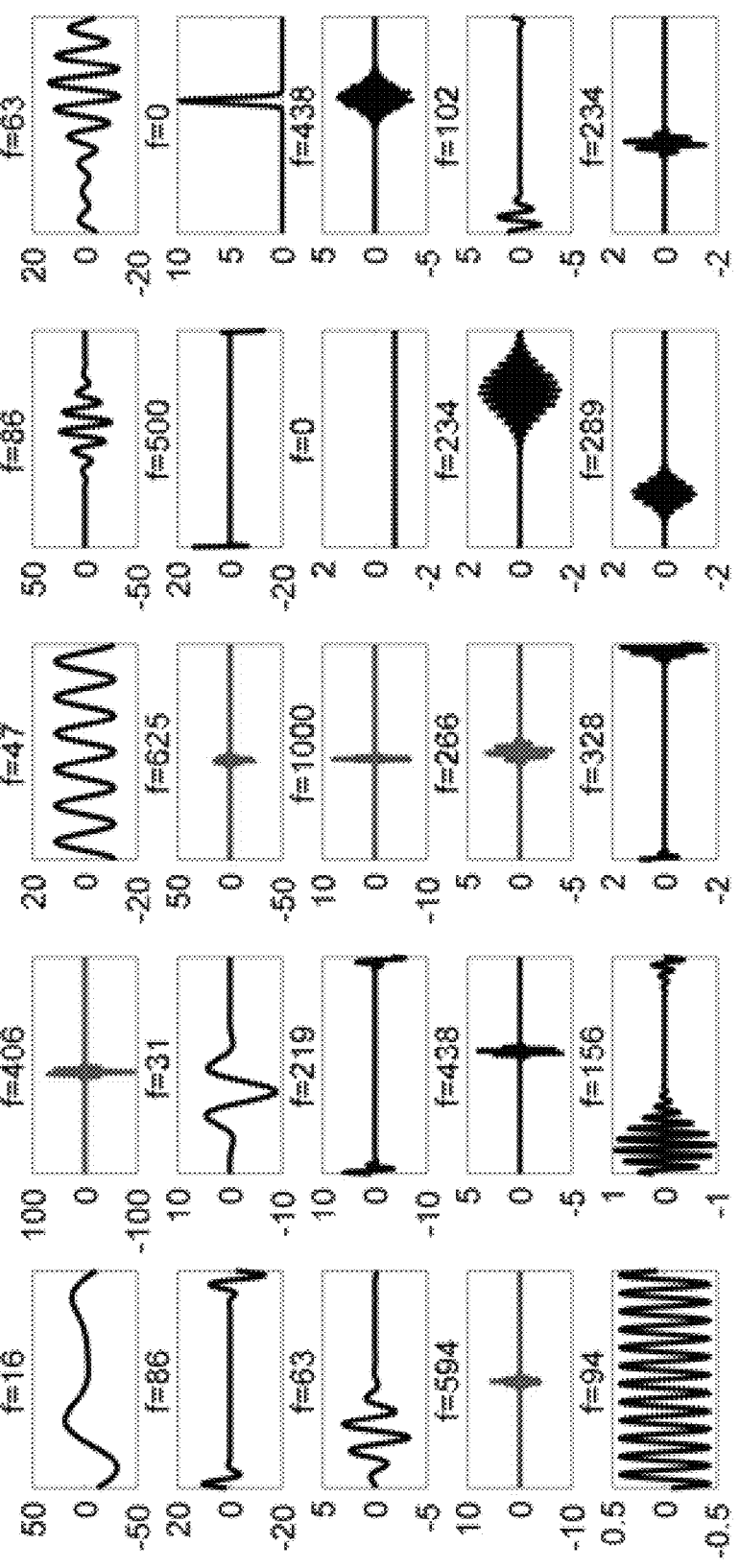
Figures 6B, 6C:
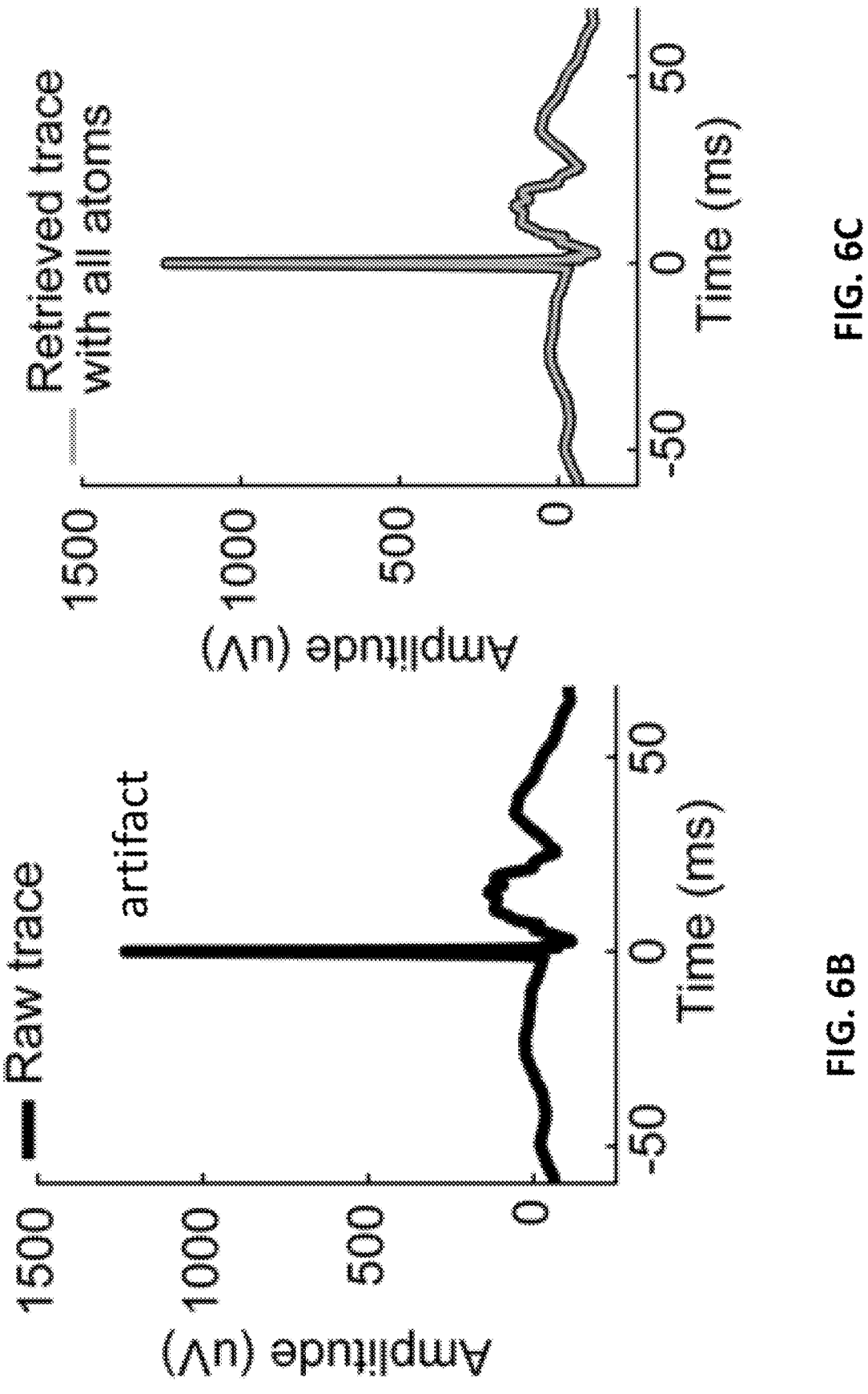
FIG. 6B is a graph showing a raw neural signal trace containing a stimulation artifact.
FIG. 6C is a graph comparing the raw neural signal trace of FIG. 6B (black line) and a signal reconstructed using the matching pursuit method and the atoms of FIG. 5A as disclosed herein (red line).
Figures 6D, 6E:
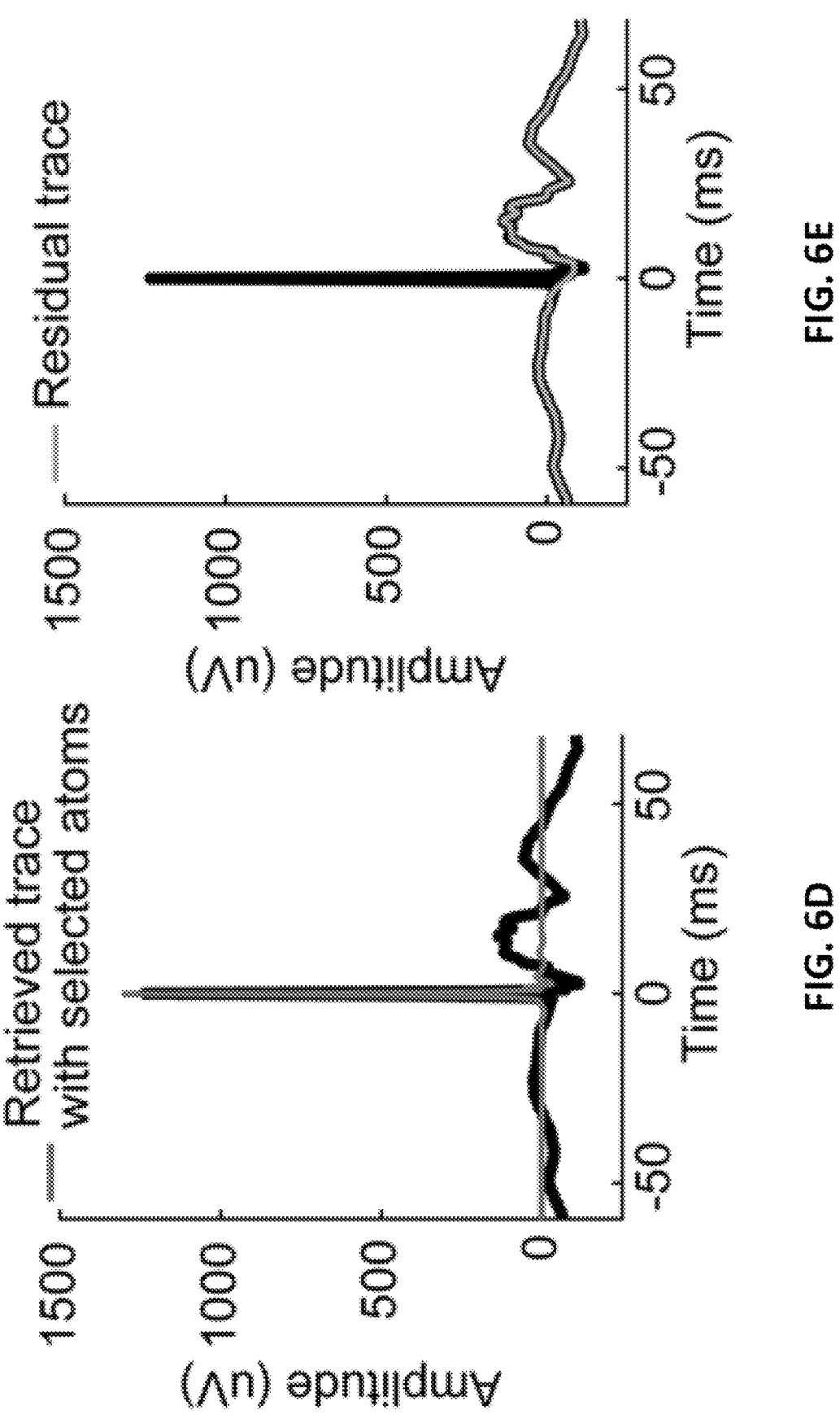
FIG. 6D is a graph comparing the raw neural signal trace of FIG. 6B (black line) and a signal reconstructed using the matching pursuit method and only the atoms shown in red in FIG. 5A as disclosed herein; the atoms shown in red in FIG. 6A satisfy several criteria used to identify a stimulation artifact as disclosed herein.
FIG. 6E is a graph comparing the raw neural signal trace of FIG. 6B (black line) and a residual signal trace produced by removing the red signal trace of FIG. 6D from the raw signal trace of FIG. 6B.

By way of non-limiting example, FIGS. 6A, 6B, 6C, 6D, and 6E illustrate the method for removing stimulation artifacts from a neural signal trace as disclosed herein. The method includes decomposing a raw signal trace, shown in FIG. 6B into a plurality of atoms. FIG. 6A contains graphs of 50 atoms selected using the MP algorithm for the linear decomposition of the raw signal trace containing a signal artifact (FIG. 6B). FIG. 6C compares the raw signal trace (black) to a trace reconstructed using all 50 atoms shown in FIG. 6A (orange line); the reconstructed trace (orange line) is highly similar to the raw trace (black line). The method further includes identifying and selecting a subset of the atoms of the MP-generated decomposition according to the three criteria described above (centered around stimulation onsite time, <70 Hz/Dirac, and short duration). The atoms of the decomposition identified using these criteria are denoted as red traces in FIG. 6A. FIG. 6D shows a signal trace reconstructed by adding the atoms associated with the stimulation artifact (i.e. the red traces of FIG. 6A. The red signal trace shown in FIG. 6D represents the stimulation artifact identified by the disclosed method. The disclosed method further includes determining a clean trace (or residual trace) by subtracting the stimulation artifact shown in FIG. 6D from the raw signal trace shown in FIG. 6B. FIG. 6E shows a comparison of the clean trace (green) and the raw signal trace (black).

Figure 7A:
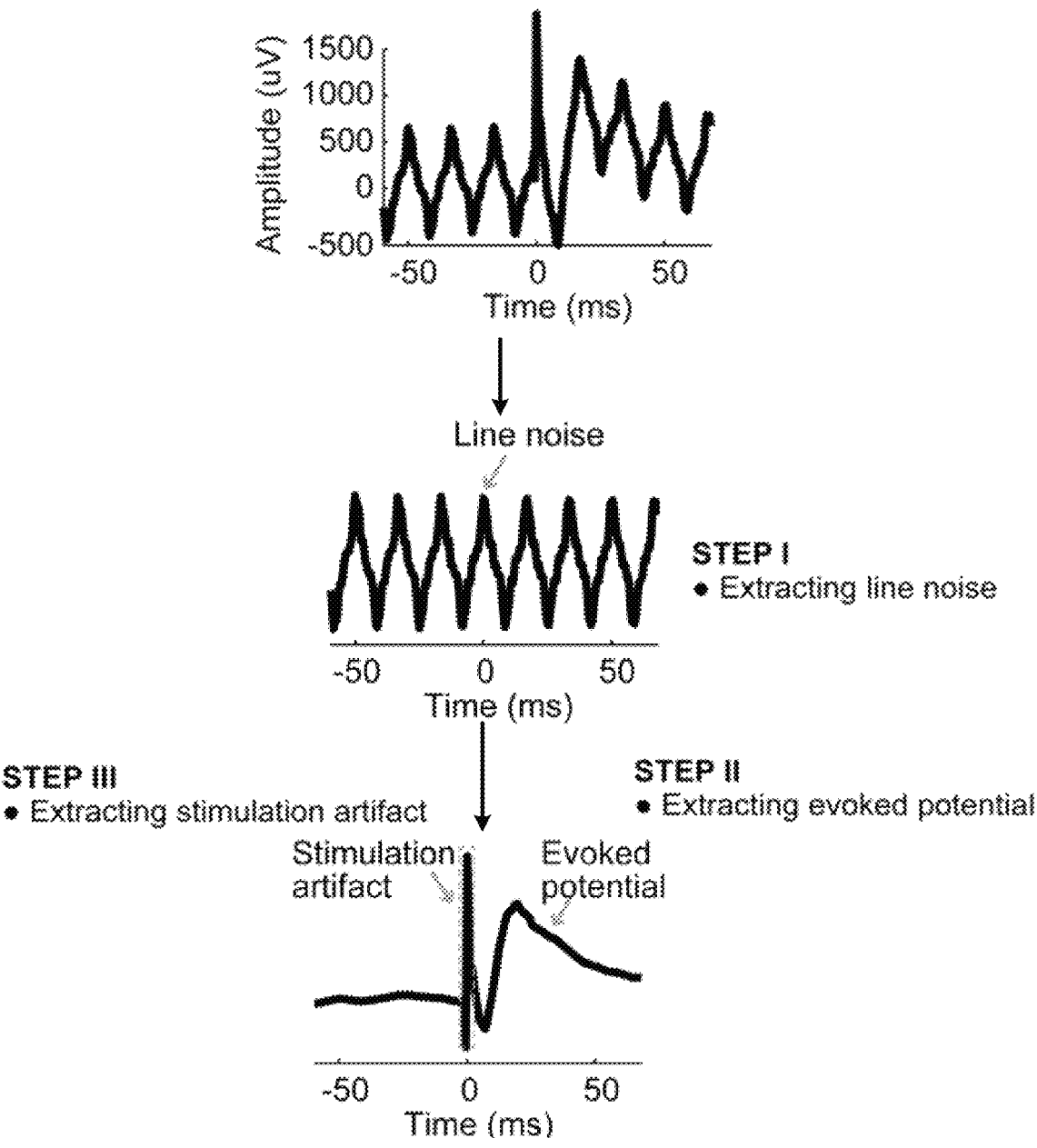
FIG. 7A is a series of graphs illustrating an overview of a method of removing line noise (middle graph) and stimulation artifacts (bottom graph) from a raw neural signal trace (top graph) as disclosed herein.
Figure 7B:
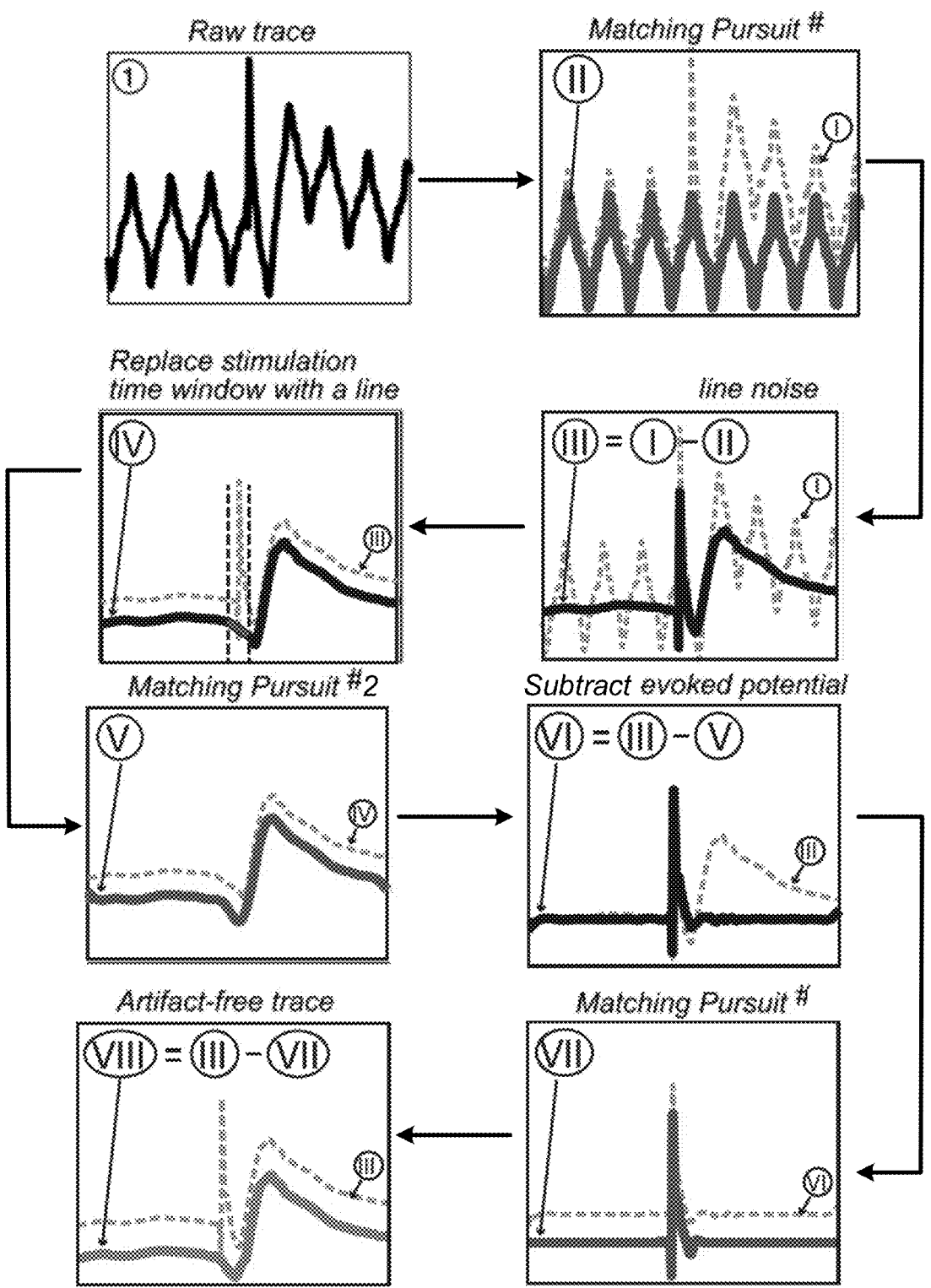
FIG. 7B is a flowchart with graphs illustrating the steps of the method illustrated in FIG. 7A.

By way of another non-limiting example, FIGS. 7A and 7B illustrate the disclosed method of removing brain stimulation artifacts from neural recordings in another aspect. FIG. 7A is a schematic overview of the disclosed method in this aspect. The method includes receiving a raw neural signal trace (top graph) that may include a superposition of signals indicative of a variety of phenomena including, but not limited to, a stimulation evoked potential, a stimulation artifact, and line noise. As illustrated in FIG. 7A, to remove the stimulation artifact using the disclosed method in this aspect, the line noise is removed, followed by the removal of the evoked potential, and finally the removal of the stimulation artifact.

In this example, the steps of the method illustrated in FIG. 7A are implemented by decomposing the raw signal into a plurality of atoms using the MP algorithm as described herein and then selecting and removing subsets of the plurality of atoms associated with each of the three signal subsets (line noise, stimulation evoked potential, and stimulation artifact) as identified by specific criteria defining the characteristics of the atoms associated with each signal subset. Without being limited to any particular theory, the line noise within the raw signal trace is removed using the MP-based method as described herein to avoid spectral leakage associated with the use of other existing methods of noise removal such as notch filtering (see FIG. 5C, middle graph). Further, because the frequency components of the stimulation evoked potential (EP) are complex and may overlap with the corresponding frequency components of the stimulation artifact trace, the EP is removed from the signal trace prior to extracting the stimulation artifact trace from the residual signal remaining after removing the EP (i.e., without EP). To maintain an intact EP signal, the stimulation artifact is subtracted from the signal trace with only the line noise removed to produce a clean signal trace that contains just the EP with the line noise and stimulation artifact removed.

FIG. 7B is a flow chart illustrating the specific steps of the method illustrated in FIG. 7A. As illustrated in FIG. 3B, the method includes receiving a raw signal trace at (1) and performing MP to decompose the raw signal trace into a plurality of atoms. At (2) a subset of the plurality of atoms from (1) is selected according to a set of line noise criteria. The subset of the plurality of atoms is summed to produce a line noise trace (red line), shown superimposed over the raw signal trace (dashed) at (2). In some aspects, the line noise criteria for selecting atoms associated with line noise include atoms with frequencies larger than about 55 Hz, and long atoms that extend along the entire time axis.

Referring again to FIG. 7B, the red signal trace associated with line noise is subtracted from the raw signal trace at (3) to produce a second signal trace that includes the EP and the stimulation artifact, but not the signal noise. The second signal trace without line noise is determined at (3) by subtracting the line noise trace (2) from the raw signal trace (1), i.e. (3)=(1)-(2). At (4) the stimulation time window in the second trace is replaced with a straight line (red portion) and then MP is performed on the resulting third signal trace at (5) to decompose the third signal trace into a second plurality of atoms. A subset of the second plurality of atoms associated with the EP is selected according to a set of EP criteria that includes, but is not limited to, those atoms with frequencies of less than about 70 Hz. The subset of the second plurality of atoms is summed to produce an EP signal trace (red line), shown compared to the third signal trace from (4) (dashed line). The EP signal trace of (5) is subtracted from the second signal trace of (3) to produce a fourth signal trace at (6). The fourth signal trace is decomposed into a third plurality of atoms at (7). A subset of the third plurality of atoms associated with the stimulation artifact is selected according to the stimulation artifact criteria, including, but not limited to, atoms centered around the stimulation onset time, atoms with frequencies greater than about 70 Hz or a Dirac atom, and a short atom that does not extend along the entire time axis. (short atom). The subset of the third plurality of atoms is summed to produce the stimulation artifact trace (red) shown compared to the fourth signal trace at (7).

Referring again to FIG. 7B, the stimulation artifact trace is subtracted from the second signal trace without line noise at (8) to produce an artifact-free trace (green). After these procedures, only the line noise from (2) and the stimulation artifact from (7) have been removed from the raw trace, while all other brain signals remain intact within the artifact-free trace.

Figure 15:
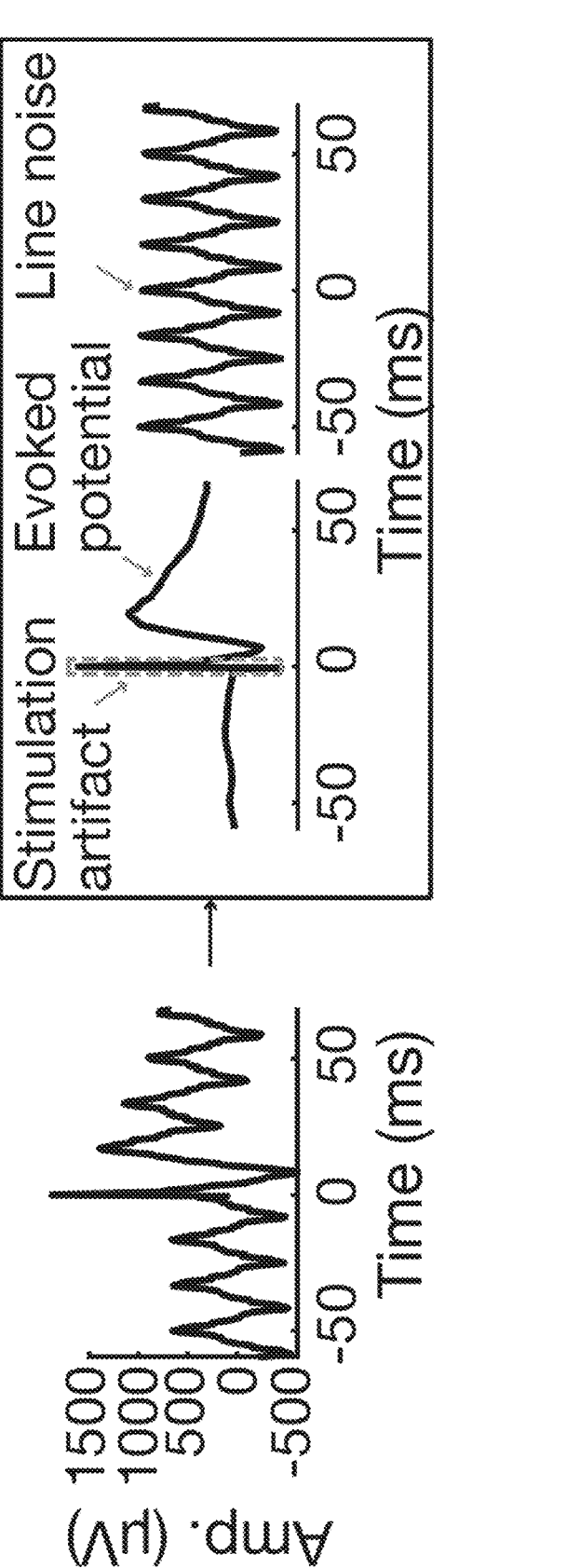
FIG. 15 is a graphical illustration of three types of artifacts removed from electrophysiological measurements of brain activity using the MPARRM method disclosed herein.

The recorded signal during electrical stimulation typically has three major components (FIGS. 7A and 15), which are electrical line noise, stimulation artifact, and the electrophysiologic activity. It has proven difficult to remove stimulation artifacts and line noise from recorded signals without losing information from the electrophysiologic signal components. We therefore developed a matching pursuit algorithm (MP) to accomplish this task without the same limitations of previously published approaches.

By way of another non-limiting example, the MP algorithm is an iterative procedure that decomposes a signal including, but not limited to, electrophysiological signals, to a linear combination of basis functions, referred to herein as "atoms". Without being limited to any particular theory, Gabor, sharp Gaussian, Dirac (1 at t=0; otherwise 0), and Fourier (pure sinusoids) atoms are useful as basis functions in the signal decomposition of electrophysiological signals obtained during SPEP stimulation. Without being limited to any particular theory, Gabor atoms provide a good compromise between frequency and time resolution, sharp Gaussian and Dirac atoms are useful to represent sharp and transient signals, and Fourier atoms are useful to represent periodic signals such as line noise.

In this non-limiting example, the denoising procedure by which MPARRM extracts stimulation artifacts can be broken into seven steps, whose signals are represented by Roman numeral I-VII in FIG. 7D. The line noise (e.g., 60 Hz and harmonics) can be represented by long atoms that are spread along the time axis and concentrated at their characteristic frequencies which are eliminated from the signal in steps 1 (matching pursuit #1) and 2 (subtract line noise). Without being limited to any particular theory, this procedure is more powerful than traditional notch filtering, which can create strong artifactual oscillations around sharp stimulation artifacts. Such filtering can obscure strong potentials induced shortly after stimulation, such as early negative potentials (N1) occurring at 10-50 ms. Evoked potentials are temporally removed from the signal at steps 3 (replace stimulation time window with a line), 4 (matching pursuit #2, and 5 (subtract evoked potential) to ensure they are not falsely identified as a stimulation artifact. Finally, the stimulation artifact is extracted after the line noise and evoked potential have been removed in steps 6 (matching pursuit #3) and 7 ((artifact-free trace). In various aspects, the stimulation artifact is represented by atoms including, but not limited to, short Gabor, short Gaussian, and Dirac atoms at the time of stimulation onset. Table 2 summarized the steps of the disclosed MPARRM method in some aspects; the steps in Table 2 refer to portions of FIG. 7B. The criteria used for the MP phases of the method of TABLE 1 are summarized in TABLE23.

TABLE 1

MPARRM Method Steps

| Step | Signal Processing |
|------|-------------------|
| 1 | Decomposing the raw trace (I) using the MP algorithm and reconstructing the line noise (II) based on criterion #1 |
| 2 | Removing the line noise from the raw trace (i.e., III = I-II) |
| 3 | Interpolating the stimulation time window with a straight line from 2.5 ms preceding to 2.5 ms following stimulation onset (IV) |
| 4 | Decomposing the interpolated trace with MP algorithm and reconstructing the evoked potential (V) based on criterion #2 |
| 5 | Removing the evoked potential from trace-III (i.e., VI = III-V) |
| 6 | Decomposing the residual signal (VI) with MP algorithm and reconstructing the stimulation artifact (VII) based on criterion #3. Specifically, the center time of the atom is within the artifact window (i.e., 5 ms preceding and 5 ms following stimulation onset); |
| 7 | Removing the stimulation artifact from trace-III (i.e., VIII = III-VII). The green trace (VIII) represents the final clean signal. The line noise and the stimulation artifacts are removed, while the brain signals (including the evoked potentials) are reserved |

TABLE 2

Criterion For Matching Pursuit Atoms

| Criterion | MP to Remove | Limitations for Atoms Selected by MP |
|-----------|--------------|--------------------------------------|
| 1 | Line Noise | Atom frequency >55 Hz Atom is spread along the whole time axis, i.e., long atom |
| 2 | Evoked Potential | Atom frequency <70 Hz |
| 3 | Stimulation Artifact | Atom duration is centered around stimulation onset Atom frequency >70 Hz or is Dirac atom; Atom is not spread along the whole time axis, i.e., short atom. |

Figures 8A, 8B:
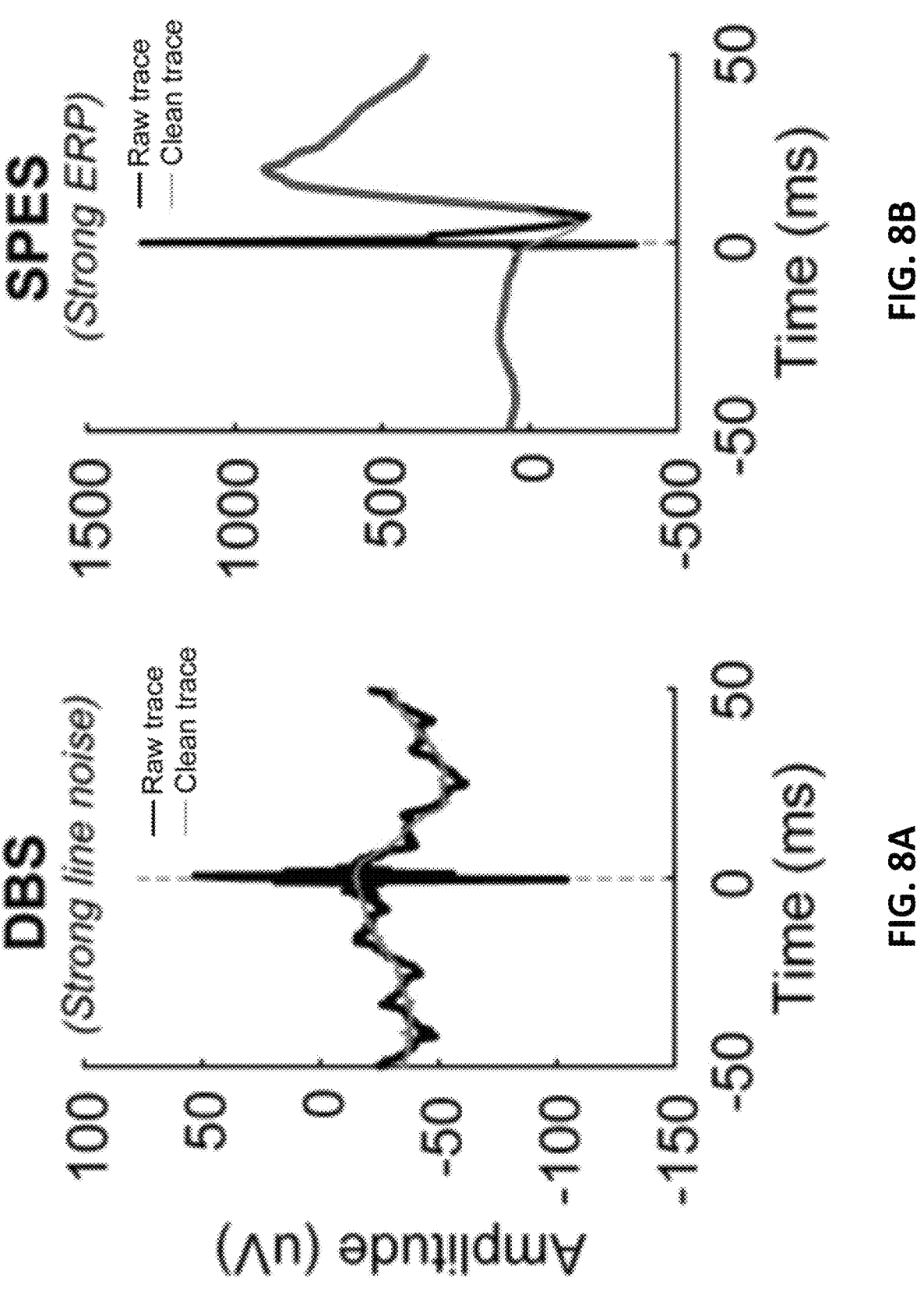
FIG. 8A shows one trace of an electroencephalographic signal (black line) near the human parietal-frontal areas with 1 Hz of DBS in the thalamic nucleus.
FIG. 8B shows one stereo-electroencephalographic signal (black line) near the human hippocampus with 1 Hz of single-pulse electrical stimulation in the amygdala.
Figures 8C, 8D:
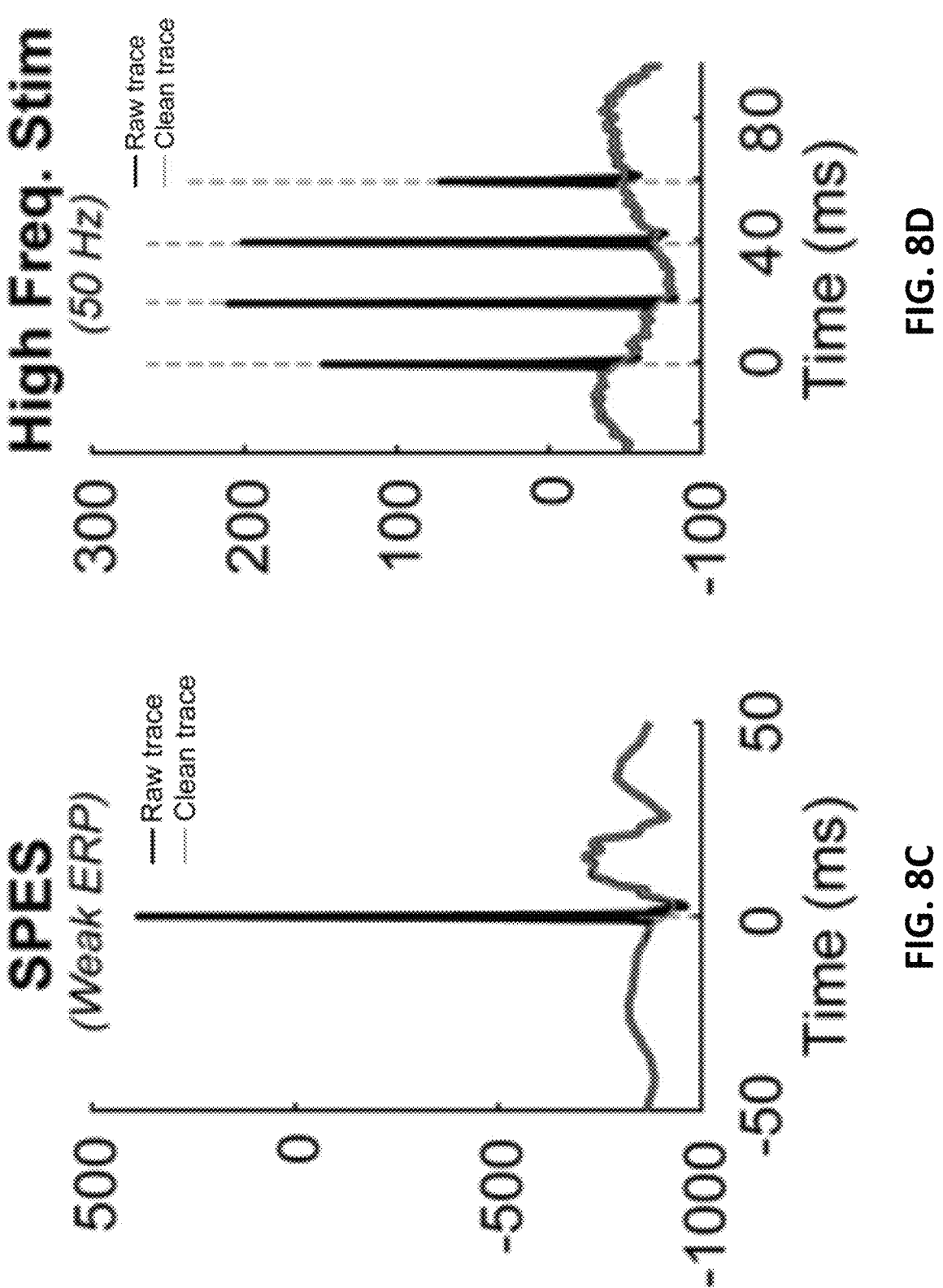
FIG. 8C shows one stereo-electroencephalographic signal (black line) near the human temporal lobe with 1 Hz of single-pulse electrical stimulation in the amygdala.
FIG. 8D shows one stereo-25 electroencephalographic signal (black line) near the human frontal lobe with 50-Hz high-frequency electrical stimulation in the amygdala.
Figure 8E:
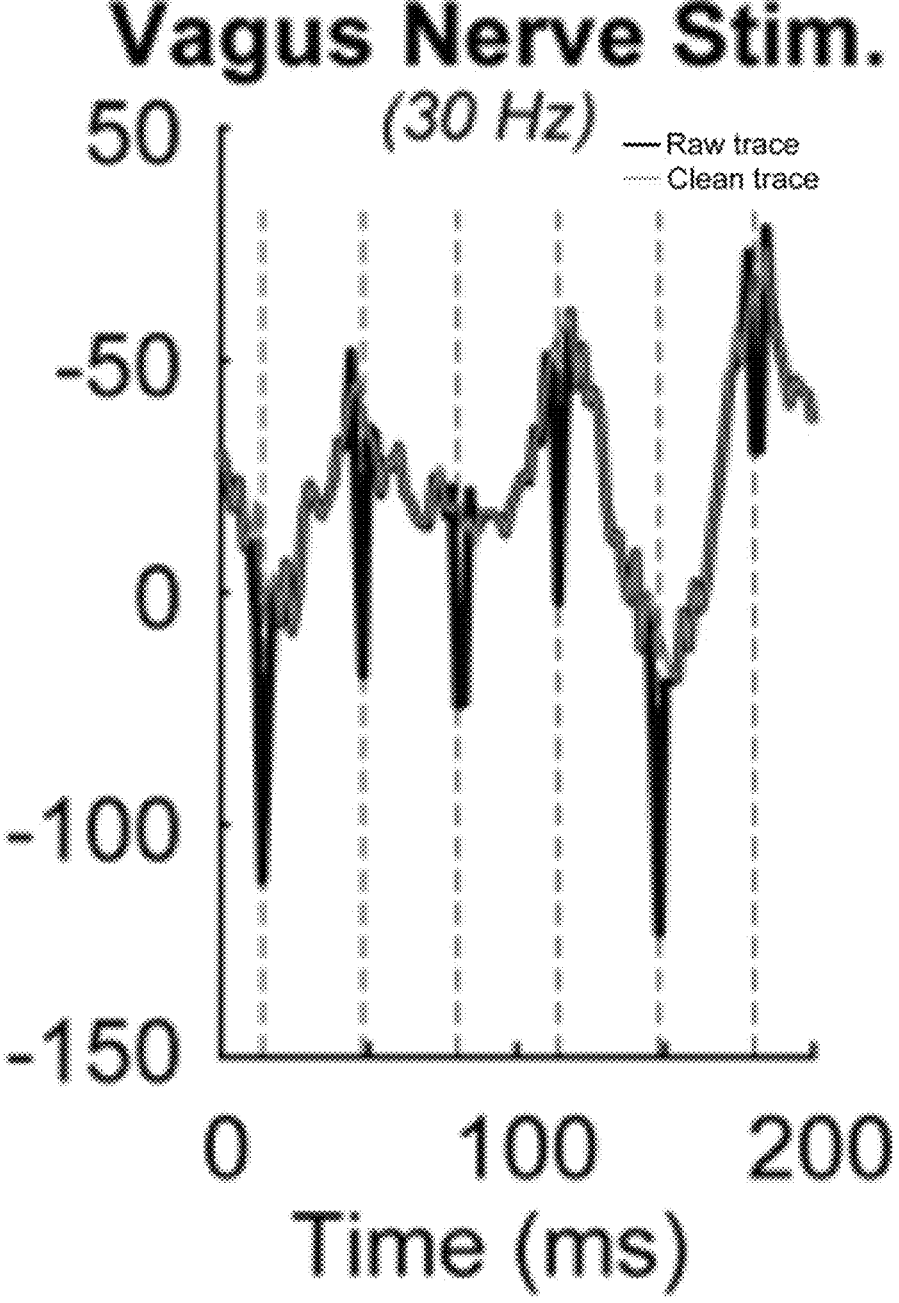
FIG. 8E shows one stereo-electroencephalographic signal (black line) in the human frontal brain area with 30 Hz vagus nerve stimulation.

FIGS. 8A, 8B, 8C, 8D, and 8E contain a series of graphs comparing clean traces (green) resulting from the application of the disclosed method for the purpose of removing stimulation artifacts. All the black lines indicate the raw trace, and the green lines indicate the artifact-free signal after applying our novel method. FIG. 8A shows one trace of an electroencephalographic signal (black line) near the human parietal-frontal areas with 1 Hz of DBS in the thalamic nucleus. FIG. 8B shows one stereo-electroencephalographic signal (black line) near the human hippocampus with 1 Hz of single-pulse electrical stimulation in the amygdala. FIG. 8C shows one stereo-electroencephalographic signal (black line) near the human temporal lobe with 1 Hz of single-pulse electrical stimulation in the amygdala. FIG. 8D shows one stereo-25 electroencephalographic signal (black line) near the human frontal lobe with 50-Hz high-frequency electrical stimulation in the amygdala. FIG. 8E shows one stereo-electroencephalographic signal (black line) in the human frontal brain area with 30 Hz vagus nerve stimulation.

In various aspects, the disclosed method is configured to extract artifacts from neural signals obtained in association with multiple kinds of brain stimulation, including, but not limited to, rTMS, single-pulse TMS, tDCS, tRNS, tACS, tFUS, VNS, SEPS, high-frequency stimulation, and microstimulation.

In various aspects, the computer-implemented methods disclosed herein are implemented using various computing devices and systems that include computing devices as described herein.

FIG. 1 depicts a simplified block diagram of the system for implementing the computer-aided methods of removing stimulation artifacts from neural signals as described herein. As illustrated in FIG. 1, the computing device 300 may be configured to implement at least a portion of the tasks associated with implementing the methods described herein. The computer system 300 may include a computing device 302. In one aspect, the computing device 302 is part of a server system 304, which also includes a database server 306. The computing device 302 is in communication with a database 308 through the database server 306. The computing device 302 is communicably coupled to a user computing device 330 through a network 350. The network 350 may be any network that allows local area or wide area communication between the devices. For example, the network 350 may allow communicative coupling to the Internet through at least one of many interfaces including, but not limited to, at least one of a network, such as the Internet, a local area network (LAN), a wide area network (WAN), an integrated services digital network (ISDN), a dial-up-connection, a digital subscriber line (DSL), a cellular phone connection, and a cable modem. The user computing device 330 may be any device capable of accessing the Internet including, but not limited to, a desktop computer, a laptop computer, a personal digital assistant (PDA), a cellular phone, a smart-phone, a tablet, a phablet, wearable electronics, smartwatch, or other web-based connectable equipment or mobile devices.

Figure 2:
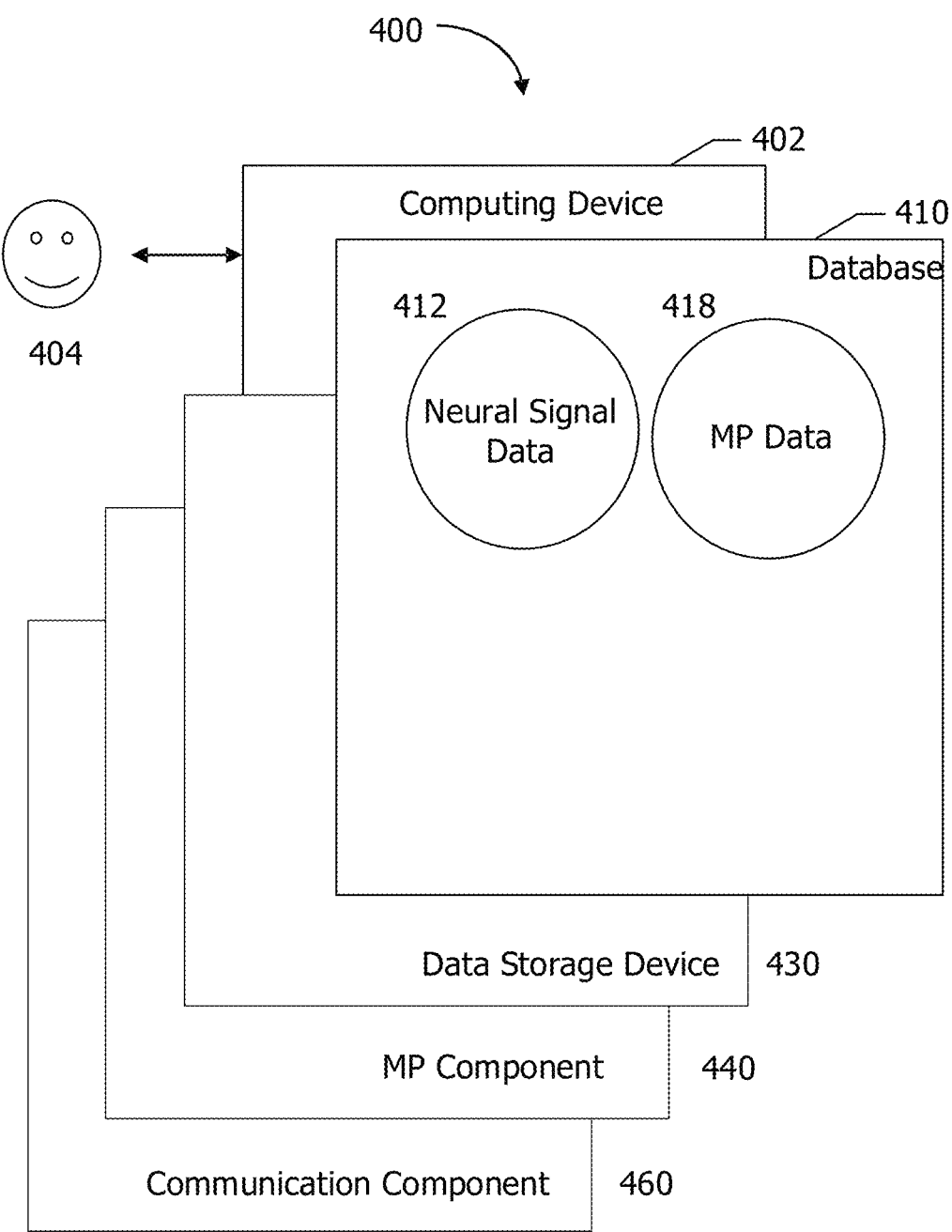
FIG. 2 is a block diagram schematically illustrating a computing device in accordance with one aspect of the disclosure.

In other aspects, the computing device 302 is configured to perform a plurality of tasks associated with the disclosed methods. FIG. 2 depicts a component configuration 400 of computing device 402, which includes database 410 along with other related computing components. In some aspects, computing device 402 is similar to computing device 302 (shown in FIG. 1). A user 404 may access components of computing device 402. In some aspects, database 410 is similar to database 308 (shown in FIG. 1).

In one aspect, database 410 includes neural signal data 412 and matching pursuit (MP) data 418. Non-limiting examples of suitable neural signal data 412 include any values of parameters defining the raw neural signal traces, clean signal traces, and/or the intermediate signal traces generated during implementation of the disclosed method as described herein. In one aspect, the MP data 412 includes any values defining the atoms used to decompose the signal traces, the selection criteria used to select subsets of the pluralities of atoms defining a decomposed signal trace, and any other parameters associated with the implementation of the MP algorithm to practice the method as described herein.

Computing device 402 also includes a number of components that perform specific tasks. In an exemplary aspect, computing device 402 includes a data storage device 430, matching pursuit (MP) component 440, and communication component 460. Data storage device 430 is configured to store data received or generated by computing device 402, such as any of the data stored in database 410 or any outputs of processes implemented by any component of computing device 402.

In various aspects, the matching pursuit (MP) component 440 is configured to implement the matching pursuit algorithm and to implement the method of removing stimulation artifacts from neural signals using the matching pursuit algorithm, selection of atom subsets, and reconstruction/removal of signal subsets as described herein.

Communication component 460 is configured to enable communications between computing device 402 and other devices (e.g. user computing device 330 shown in FIG. 1) over a network, such as a network 350 (shown in FIG. 1), or a plurality of network connections using predefined network protocols such as TCP/IP (Transmission Control Protocol/Internet Protocol).

Figure 3:
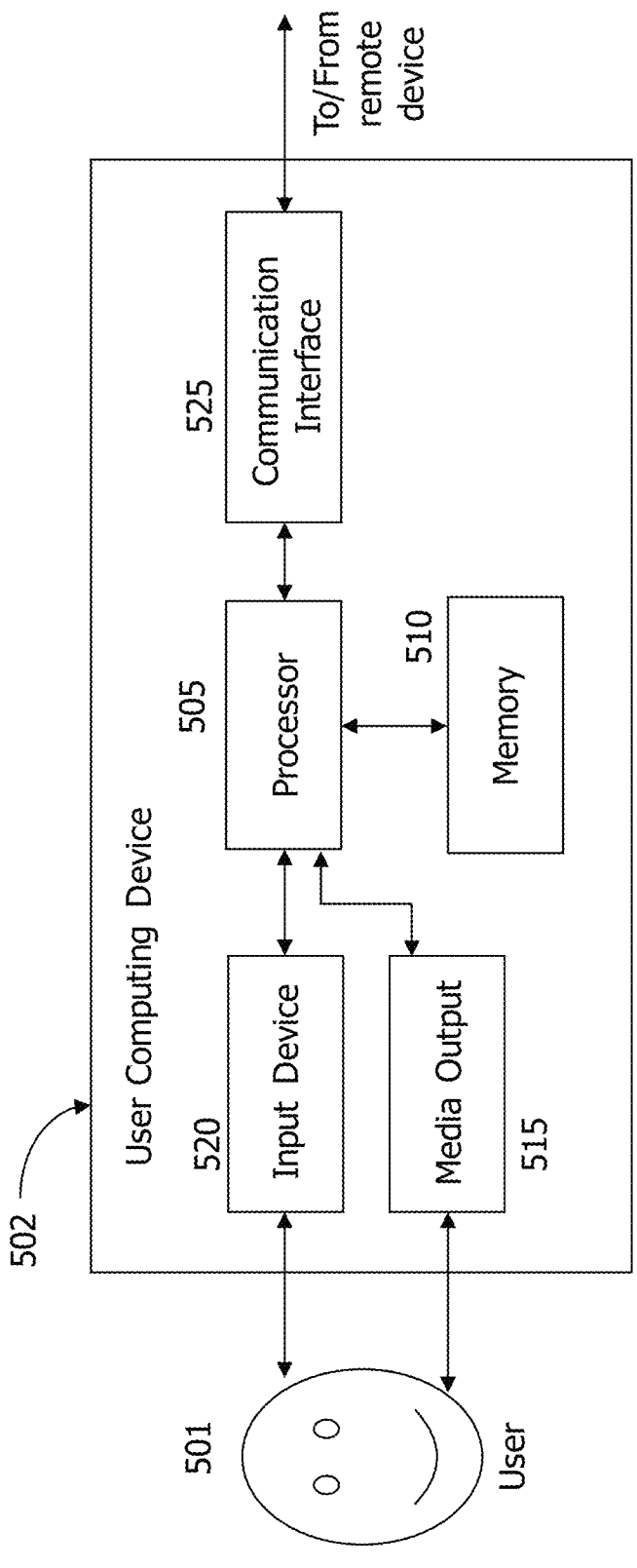
FIG. 3 is a block diagram schematically illustrating a remote or user computing device in accordance with one aspect of the disclosure.

FIG. 3 depicts a configuration of a remote or user computing device 502, such as user computing device 330 (shown in FIG. 1). Computing device 502 may include a processor 505 for executing instructions. In some aspects, executable instructions may be stored in a memory area 510. Processor 505 may include one or more processing units (e.g., in a multi-core configuration). Memory area 510 may be any device allowing information such as executable instructions and/or other data to be stored and retrieved. Memory area 510 may include one or more computer-readable media.

Computing device 502 may also include at least one media output component 515 for presenting information to a user 501. Media output component 515 may be any component capable of conveying information to user 501. In some aspects, media output component 515 may include an output adapter, such as a video adapter and/or an audio adapter. An output adapter may be operatively coupled to processor 505 and operatively coupleable to an output device such as a display device (e.g., a liquid crystal display (LCD), organic light-emitting diode (OLED) display, cathode ray tube (CRT), or "electronic ink" display) or an audio output device (e.g., a speaker or headphones). In some aspects, media output component 515 may be configured to present an interactive user interface (e.g., a web browser or client application) to user 501.

In some aspects, computing device 502 may include an input device 520 for receiving input from user 501. Input device 520 may include, for example, a keyboard, a pointing device, a mouse, a stylus, a touch-sensitive panel (e.g., a touchpad or a touch screen), a camera, a gyroscope, an accelerometer, a position detector, and/or an audio input device. A single component such as a touch screen may function as both an output device of media output component 515 and input device 520.

Computing device 502 may also include a communication interface 525, which may be communicatively coupleable to a remote device. Communication interface 525 may include, for example, a wired or wireless network adapter or a wireless data transceiver for use with a mobile phone network (e.g., Global System for Mobile communications (GSM), 3G, 4G or Bluetooth) or other mobile data network (e.g., Worldwide Interoperability for Microwave Access (WIMAX)).

Stored in memory area 510 are, for example, computer-readable instructions for providing a user interface to user 501 via media output component 515 and, optionally, receiving and processing input from input device 520. A user interface may include, among other possibilities, a web browser and client application. Web browsers enable users 501 to display and interact with media and other information typically embedded on a web page or a website from a web server. A client application allows users 501 to interact with a server application associated with, for example, a vendor or business.

Figure 4:
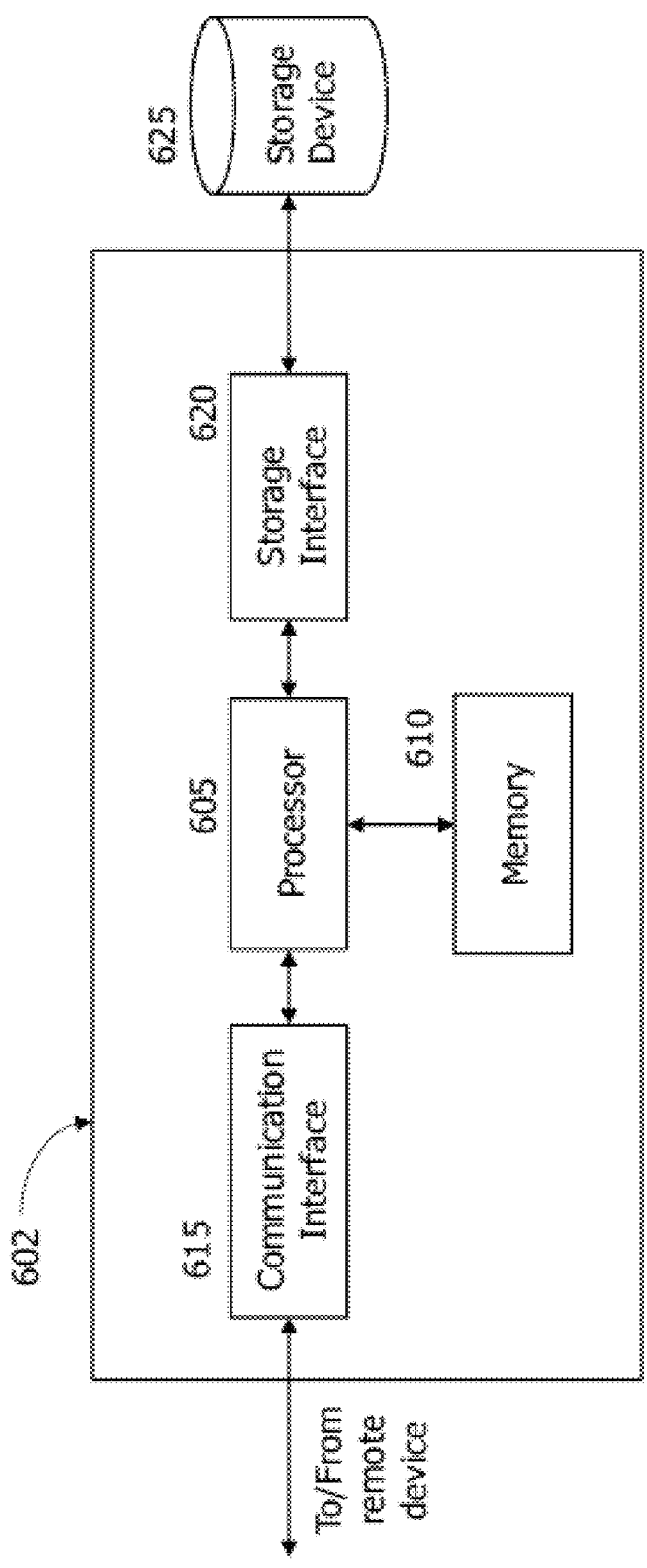
FIG. 4 is a block diagram schematically illustrating a server system in accordance with one aspect of the disclosure.

FIG. 4 illustrates an example configuration of a server system 602. Server system 602 may include, but is not limited to, database server 306 and computing device 302 (both shown in FIG. 1). In some aspects, server system 602 is similar to server system 304 (shown in FIG. 1). Server system 602 may include a processor 605 for executing instructions. Instructions may be stored in a memory area 625, for example. Processor 605 may include one or more processing units (e.g., in a multi-core configuration).

Processor 605 may be operatively coupled to a communication interface 615 such that server system 602 may be capable of communicating with a remote device such as user computing device 330 (shown in FIG. 1) or another server system 602. For example, communication interface 615 may receive requests from user computing device 330 via a network 350 (shown in FIG. 1).

Processor 605 may also be operatively coupled to a storage device 625. Storage device 625 may be any computer-operated hardware suitable for storing and/or retrieving data. In some aspects, storage device 625 may be integrated into server system 602. For example, server system 602 may include one or more hard disk drives as storage device 625. In other aspects, storage device 625 may be external to server system 602 and may be accessed by a plurality of server systems 602. For example, storage device 625 may include multiple storage units such as hard disks or solid-state disks in a redundant array of inexpensive disks (RAID) configuration. Storage device 625 may include a storage area network (SAN) and/or a network attached storage (NAS) system.

In some aspects, processor 605 may be operatively coupled to storage device 625 via a storage interface 620. Storage interface 620 may be any component capable of providing processor 605 with access to storage device 625. Storage interface 620 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 605 with access to storage device 625.

Memory areas 510 (shown in FIG. 3) and 610 may include, but are not limited to, random access memory (RAM) such as dynamic RAM (DRAM) or static RAM (SRAM), read-only memory (ROM), erasable programmable read-only memory (EPROM), electrically erasable programmable read-only memory (EEPROM), and nonvolatile RAM (NVRAM). The above memory types are examples only, and are thus not limiting as to the types of memory usable for the storage of a computer program.

The computer systems and computer-aided methods discussed herein may include additional, less, or alternate actions and/or functionalities, including those discussed elsewhere herein. The computer systems may include or be implemented via computer-executable instructions stored on non-transitory computer-readable media. The methods may be implemented via one or more local or remote processors, transceivers, servers, and/or sensors (such as processors, transceivers, servers, and/or sensors mounted on vehicle or mobile devices, or associated with smart infrastructure or remote servers), and/or via computer-executable instructions stored on non-transitory computer-readable media or medium.

In some aspects, a computing device is configured to implement machine learning, such that the computing device "learns" to analyze, organize, and/or process data without being explicitly programmed. Machine learning may be implemented through machine learning (ML) methods and algorithms. In one aspect, a machine learning (ML) module is configured to implement ML methods and algorithms. In some aspects, ML methods and algorithms are applied to data inputs and generate machine learning (ML) outputs. Data inputs may include but are not limited to images or frames of a video, object characteristics, and object categorizations. Data inputs may further include sensor data, image data, video data, telematics data, authentication data, authorization data, security data, mobile device data, geolocation information, transaction data, personal identification data, financial data, usage data, weather pattern data, "big data" sets, and/or user preference data. ML outputs may include but are not limited to: a tracked shape output, categorization of an object, categorization of a region within a medical image (segmentation), categorization of a type of motion, a diagnosis based on the motion of an object, motion analysis of an object, and trained model parameters ML outputs may further include: speech recognition, image or video recognition, medical diagnoses, statistical or financial models, autonomous vehicle decision-making models, robotics behavior modeling, fraud detection analysis, user recommendations and personalization, game AI, skill acquisition, targeted marketing, big data visualization, weather forecasting, and/or information extracted about a computer device, a user, a home, a vehicle, or a party of a transaction. In some aspects, data inputs may include certain ML outputs.

In some aspects, at least one of a plurality of ML methods and algorithms may be applied, which may include but are not limited to: genetic algorithms, linear or logistic regressions, instance-based algorithms, regularization algorithms, decision trees, Bayesian networks, cluster analysis, association rule learning, artificial neural networks, deep learning, dimensionality reduction, and support vector machines. In various aspects, the implemented ML methods and algorithms are directed toward at least one of a plurality of categorizations of machine learning, such as supervised learning, unsupervised learning, adversarial learning, and reinforcement learning.

The methods and algorithms of the invention may be enclosed in a controller or processor. Furthermore, methods and algorithms of the present invention, can be embodied as a computer-implemented method or methods for performing such computer-implemented method or methods, and can also be embodied in the form of a tangible or non-transitory computer-readable storage medium containing a computer program or other machine-readable instructions (herein "computer program"), wherein when the computer program is loaded into a computer or other processor (herein "computer") and/or is executed by the computer, the computer becomes an apparatus for practicing the method or methods. Storage media for containing such computer programs include, for example, floppy disks and diskettes, compact disk (CD)-ROMs (whether or not writeable), DVD digital disks, RAM and ROM memories, computer hard drives and backup drives, external hard drives, "thumb" drives, and any other storage medium readable by a computer. The method or methods can also be embodied in the form of a computer program, for example, whether stored in a storage medium or transmitted over a transmission medium such as electrical conductors, fiber optics or other light conductors, or by electromagnetic radiation, wherein when the computer program is loaded into a computer and/or is executed by the computer, the computer becomes an apparatus for practicing the method or methods. The method or methods may be implemented on a general-purpose microprocessor or on a digital processor specifically configured to practice the process or processes. When a general-purpose microprocessor is employed, the computer program code configures the circuitry of the microprocessor to create specific logic circuit arrangements. Storage medium readable by a computer includes medium being readable by a computer per se or by another machine that reads the computer instructions for providing those instructions to a computer for controlling its operation. Such machines may include, for example, machines for reading the storage media mentioned above.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application, or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing from the scope of the present disclosure defined in the appended claims. Furthermore, it should be appreciated that all examples in the present disclosure are provided as non-limiting examples.

As used herein, the term "multiple types of brain stimulation" refers to different types of both non-invasive and invasive brain stimulation techniques. Non-limiting examples of non-invasive brain stimulation include repetitive transcranial magnetic stimulation (rTMS), single-pulse TMS, transcranial direct current stimulation (tDCS), transcranial random noise stimulation (tRNS), transcranial alternating current stimulation (tACS), transcranial focused ultrasound stimulation (tFUS), vagus nerve stimulation (VNS); invasive brain stimulation including single-pulse electrical stimulation (SEPS), high-frequency stimulation, and micro-stimulation.

As used herein, the term "neural signal" refers broadly to any signal reflecting the electromagnetic (EM) activity of the brain, without limitation. Non-limiting examples of neural signals include signals indicative of electroencephalographic activity (EEG), electrocorticographic (ECoG) activity, stereo-electroencephalographic (SEEG) activity, magnetoencephalographic (MEG) activity, and local field potential (LFP) activity.

As used herein, the term "neural targets" refers broadly to any brain site that is chosen as the target of brain stimulation.

As used herein, the term "neural response" refers broadly to the neural signal that is related (or response) to the brain stimulation.

As used herein, the term "stimulation artifacts" refers broadly to the non-neural signal that is not originally from neural activity, but instead, from the stimulation.

In various aspects, the disclosed method can be used to remove stimulation artifacts from different types of stimulation techniques: including repetitive transcranial magnetic stimulation (rTMS), single-pulse TMS, transcranial direct current stimulation (tDCS), transcranial random noise stimulation (tRNS), transcranial alternating current stimulation (tACS), transcranial focused ultrasound stimulation (tFUS), vagus nerve stimulation (VNS); single-pulse electrical stimulation (SEPS), high-frequency stimulation, and micro-stimulation In various aspects, the disclosed method can be used to remove stimulation artifacts of different neural signals, including any signal reflecting the electromagnetic (EM) activity of the brain without limitation including, but not limited to, electroencephalographic activity (EEG), electrocorticographic (ECoG) activity, stereo-electroencephalographic (SEEG) activity, magnetoencephalographic (MEG) activity, and local field potential (LFP) activity.

The function dictionaries involved in the matching pursuit algorithm include any suitable functions/atoms for extracting the stimulation artifact without limitation. Non-limiting examples of suitable functions/atoms include Gabor functions, Dirac functions, Fourier functions, and Rectangle functions.

In various aspects, the frequency restriction to extract the line noise can be any frequency without limitation including, but not limited to, 55 Hz.

The frequency restriction to extract the evoked potential can be any frequency without limitation including, but not limited to, 70 Hz.

The frequency restriction to extract the stimulation artifact can be any frequency without limitation including, but not limited to, 70 Hz.

Although the present disclosure describes various criteria for selecting subsets of atoms that include particular ranges of frequencies, center times, and time spread lengths herein, any suitable selection criteria may be used without limitation. In various aspects, additional selection criteria related to a variety of atom characteristics may be used to better extract the line-noise, evoked potential, and stimulation artifact including, but not limited to, the center time of atoms, frequency of atoms, type of atoms, time spread length of atoms, and any combination thereof.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Validation of MPARRM Artifact Removal Method

To validate the disclosed MPARRM artifact removal method across a wide range of potential stimulation artifact types the following experiments were conducted. Simulated artifacts were generated using recordings from electrodes submerged in a saline solution to generate 110 types of SPES artifacts, added these artifacts to the stereo-electroencephalographic (SEEG) signals recorded from 9 human subjects during a receptive speech task, and then removed the simulated artifacts from the added signals using MPARRM. The effectiveness of MPARRM was quantified by comparing the raw SEEG signals (prior to adding artifacts) with the clean signal (SEEG signals with added simulated artifacts after MPARRM denoising).

Experimental Methods

Figure 12A:
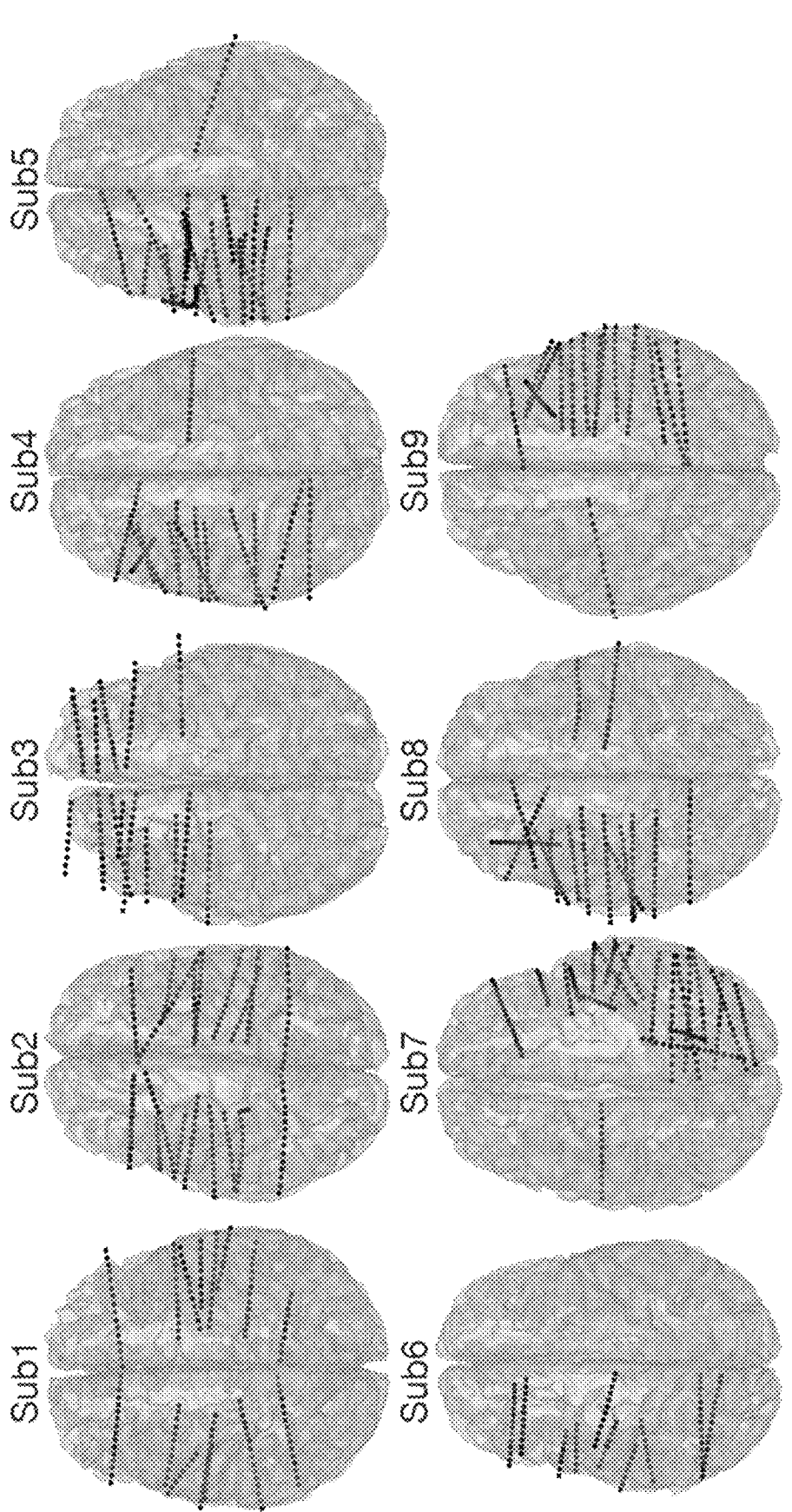
FIG. 12A contains brain images of nine human subjects participating in an auditory stimulus protocol as described in the Examples herein; Sub4 also participated in the single-pulse electrical stimulation (SPES) protocol as described in the Examples herein.

Subjects. Human SEEG Recordings and Electrode Localization SEEG signals were recorded in 9 human subjects (see FIG. 12A). Subjects underwent placement of SEEG electrodes (PMT) for Stage-2 diagnostic electrocorticography to help localize epileptogenic focus for clinical applications. Implantation was performed according to the standard of care at our institution.

SEEG signals were recorded using signal acquisition hardware and general-purpose brain-computer interface software BC12000. SEEG signals were amplified and digitized at 2000 Hz in parallel to the clinical monitoring system to ensure that clinical data collection was uninterrupted. We utilized preoperative MRI imaging to produce three-dimensional brain models with Freesurfer (http://surfer.nmr.mgh.harvard.edu) for anatomically accurate visualization. We localized implanted electrodes through co-registration of post-operative computer tomography (CT) scans using SPM (http://www.fil.ion.ucl.ac.uk/spm).

Auditory Stimulus. We used a receptive speech protocol to evoke a cortical response in all 9 subjects. The stimuli consisted of 32 unique words presented to patients via over-ear headphones (12 Hz-23.5 kHz audio bandwidth, 20 dB isolation from environmental noise). The duration of each stimulus was 700 ms, and the inter-stimulus interval was 1000 ms. The selected words were simple, meaningful verbs spoken by a female native English speaker. Stimuli were presented in two identical stimulus blocks composed of all 32 stimuli. Blocks were separated by a 20-second silent period during which the subject was instructed to relax. We defined individual trials as a 1700 ms-long interval (1000 ms preceding the stimulus onset and 1700 ms after the stimulus onset).

Figures 10A, 10B:
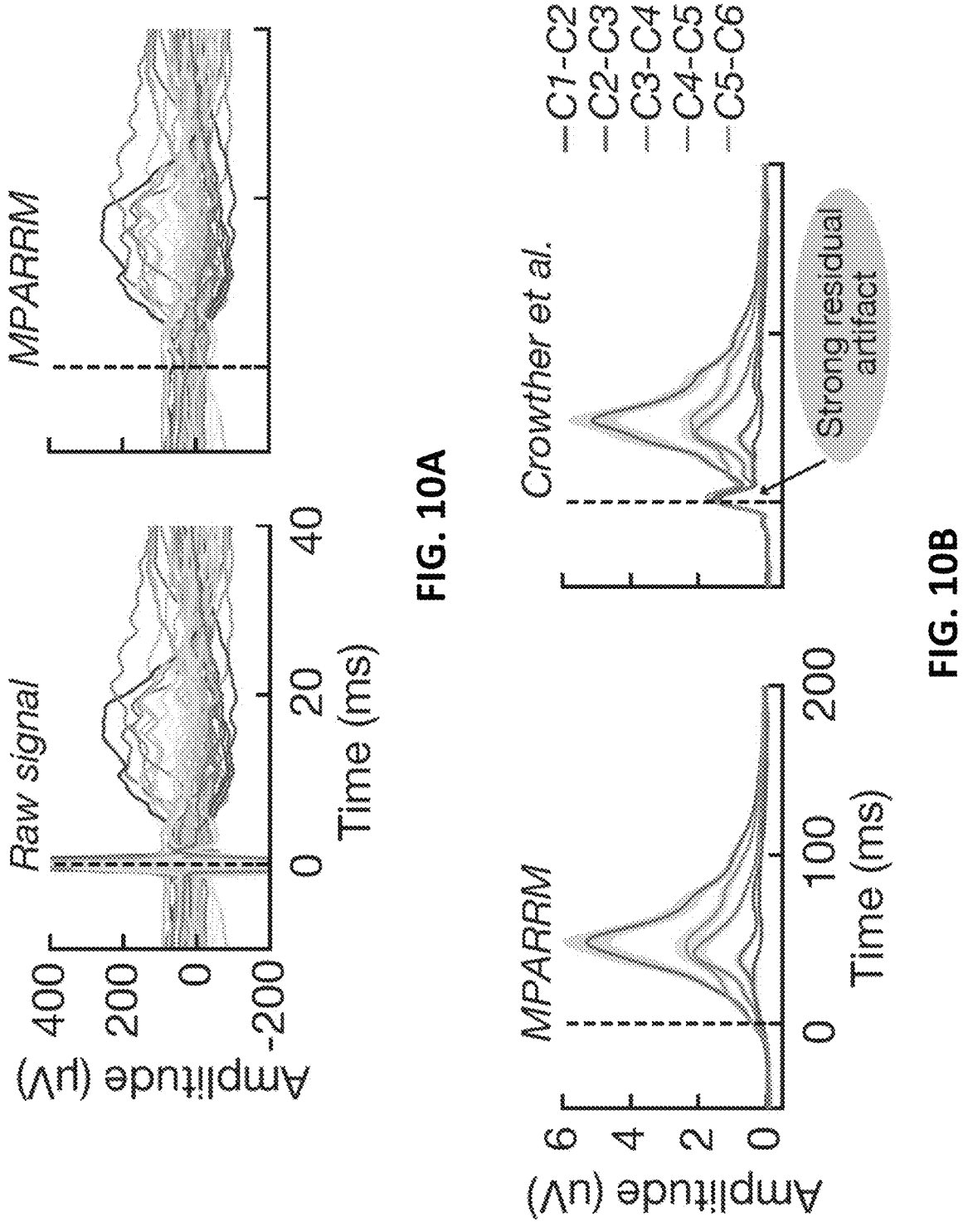
FIG. 10A summarizes the raw trial signals (left) and clean trial signals with MPARRM denoising (right) obtained from one representative electrode using human single-pulse electrical stimulation (SPES) signals.
FIG. 10B summarizes the averaged broadband gamma with MPARRM (left) and interpolate denoising (right) from additional from the trial described in FIG. 10A. The broadband gamma was averaged across all trials and all electrodes for five stimulation pairs (i.e., C1-C2, C2-C3, C3-C4, C4-C5, C5-C6) along amygdala and hippocampus.

Single-Pulse Electrical Stimulation. One human subject underwent single-pulse electrical stimulation. During SEEG recording, 200 consecutive electrical pulses (biphasic, pulse width µs, current amplitude *mA) were generated between pairs of adjacent SEEG contacts, using an inter-stimulus interval of 500 ms. This was performed across five different pairs of adjacent electrode contacts (FIGS. 10A and 10B).

Recording Stimulation Artifact in Saline. We recorded isolated SPES artifacts by suspending two standard clinical stereo-electroencephalographic (SEEG) probes (FIG. 11A) in a 0.9% saline solution. The SEEG probes (PMT, Chanhassen, Minnesota) consisted of platinum/iridium contacts 0.8 mm in diameter, spaced 3.5 mm apart (contact length 2 mm, insulation length 1.5 mm). Similar to the clinical recordings, one SEEG probe was used for stimulation and a second for recording. Both electrodes were placed in a saline bath which simulated the clinical environment to record stimulation artifacts (FIG. 11A). Stimulation was performed using a 16-channel headstage (M4016) controlled by the Intan Stim/Recording System (Intan Tech., USA). SPES was delivered through a middle contact of the first SEEG probe using a monopolar configuration. The stimulation artifact was simultaneously recorded from a middle contact of a second SEEG probe connected to a separate headstage. Stimulation was administered at 0.5 Hz with an inter-stimulus interval of 2s. 110 different biphasic pulse shapes were generated (FIGS. 11B and 11E). Stimulus parameters were based on commonly used configuration settings, and each pulse was analyzed across 60 trials. The resulting signal, which included the recurring stimulation artifacts was amplified, digitized at 30,000 Hz, and saved in the RHS file format for subsequent analysis.

To generate a template of the saline SPES artifact, we extracted the recording around each stimulus pulse (2000 ms preceding and 2000 ms following onset) and averaged the signal across all trials to reduce the background noise. We assumed the majority of the artifact was within the artifact window (1 ms preceding and 4 ms following pulse onset) and thus set the value as zeros outside of the artifact window for better comparison. We further reduced the sampling of the saline SPES artifact to 2000 Hz (MATLAB decimate( )) to match the human SEEG recordings.

Validation of MPARRM: The performance of the MPARRM method was evaluated using the combined signals from the human SEEG data and the simulated artifacts/saline data. Specifically, the human SEEG signals during the auditory stimulus trial were used as a "ground truth" signal, which ideally would be recovered by MPARRM denoising. SPES artifact from the saline recordings was added to the SEEG signal to generate a mixed pseudo-signal which simulates a SEEG study with SPEP and stimulation artifacts. The MPARRM denoising method was then applied to the mixed signal to remove the stimulation artifact. The resulting "clean" signal was then compared to the original SEEG signal, which is expected to have a strong correlation for effective denoising methods. We also applied an existing interpolate denoising method (i.e., linear merging with signals 5 ms preceding and 5 ms following stimulation onset) as a control/comparison (Crowther et al., 2019).

Figure 12B:
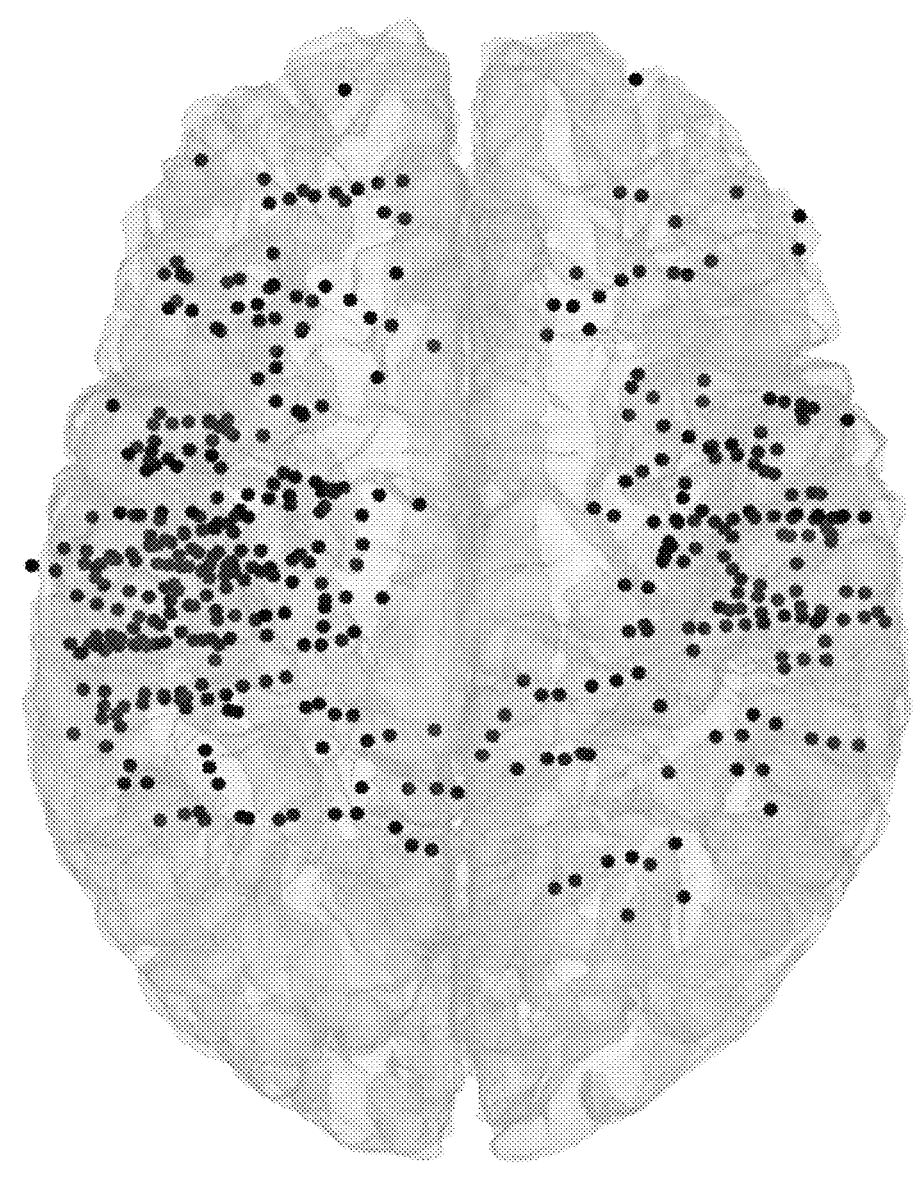
FIG. 12B contains a brain image showing the positions of all electrodes (black dots) used to obtain signals from all subjects; to reduce the computation time, we randomly selected 50 electrodes from each subject (450 electrodes in total).

We processed the human SEEG recordings by visually inspecting the signals recorded from electrodes and rejected those that exhibited potential artifacts. The signal was then high-pass filtered at 0.5 Hz to remove slow drifts. For signals obtained during the auditory stimulus trial, we re-referenced signals using a common average reference spatial filter, extracted individual trials (1000 ms preceding and 700 ms following auditory stimulus onset), and randomly selected 50 electrodes from each subject (450 electrodes in total, FIG. 12B) to reduce the computation time. For the signals obtained during the SPES trial, we re-referenced the signals using the averaged signals of electrodes that did not show strong CCEPs, and extracted the recording from each trial 500 ms preceding and 500 ms following stimulation onset.

We added the saline SPES artifact to the human SEEG recordings around 300 ms following the auditory stimulus onset, where it showed strong auditory-induced response (FIG. 9B). We validated the results within 0 to 50 ms following saline stimulation onset among various frequency bands, including theta ($\theta$, 4-7 Hz), alpha ($\alpha$, 8-12 Hz), low beta (l$\beta$, 13-20 Hz), high beta (h$\beta$, 20-30 Hz), low gamma (l$\gamma$, 30-50 Hz), and broadband gamma (b$\gamma$, 70-170 Hz). In brief, for each frequency band, we filtered the raw and clean signals (after denoising) from each electrode and took the absolute value of the Hilbert transform of the resulting signal. We then baseline-corrected and normalized the individual trials for each electrode by subtracting the average power during each trial's baseline period (500 ms to 100 ms preceding the stimulus onset), and dividing it through the standard deviation across all trial's baseline periods. We used forward-backward filters for all the filtering processes, in particular using pop eeg f iltnew( ) in EEGLAB.

Results

We added the saline SPES artifact to the human SEEG signals under auditory stimulus protocol as described above, and used the combined signal to validate the performance of the MPARRM denoising method disclosed herein both qualitatively and quantitatively. We further validated the MPARRM on human SEEG signals obtained using a single-pulse electrical signal (SPES) protocol.

Temporal and spectral effect of MPARRM. We selected a representative pulse shape (d1=100 μs, d2=100 μs, dp=100 μs, see FIGS. 11A, 11B, and 11E) to qualitatively show the results. FIG. 9A1 shows one representative trial of raw signal (grey), raw signal added with saline SPES artifact (black), and clean signal after applying MPARRM. Time 0 indicates the onset of the SPES artifact. FIG. 9A2 shows a strong ERSP increase around time 0 in the added signal (compare top left and right maps). This strong ERSP vanished after applying MPARRM (see bottom right map). However, the traditional interpolate denoising method (Crowther et al., 2019) failed to remove the artifact (see bottom left map). To evaluate the temporal difference between the raw signal and the clean signal, we calculated the absolute value of the temporal difference (subtracting the clean signal from the raw signal) within each frequency band. FIG. 9A3 shows the absolute difference value across all electrodes and all trials (mean±s.d., n=27000). The maximum absolute difference value was around time 0 with the value for each frequency band ($\theta$, $\alpha$, l$\beta$, h$\beta$, l$\gamma$, b$\gamma$) equal to 0.004, 0.006, 0.013, 0.031, 0.097, 0.702, and 0.014, 0.023, 0.049, 0.122, 0.457, 3.225 for MPARRM (FIG. 9A3, right graph) and interpolate denoising (FIG. 9A3, left graph), respectively. The interpolate denoising method showed a larger absolute difference value than MPARRM, especially for broadband gamma (3.225 vs. 0.702).

Figure 11C:
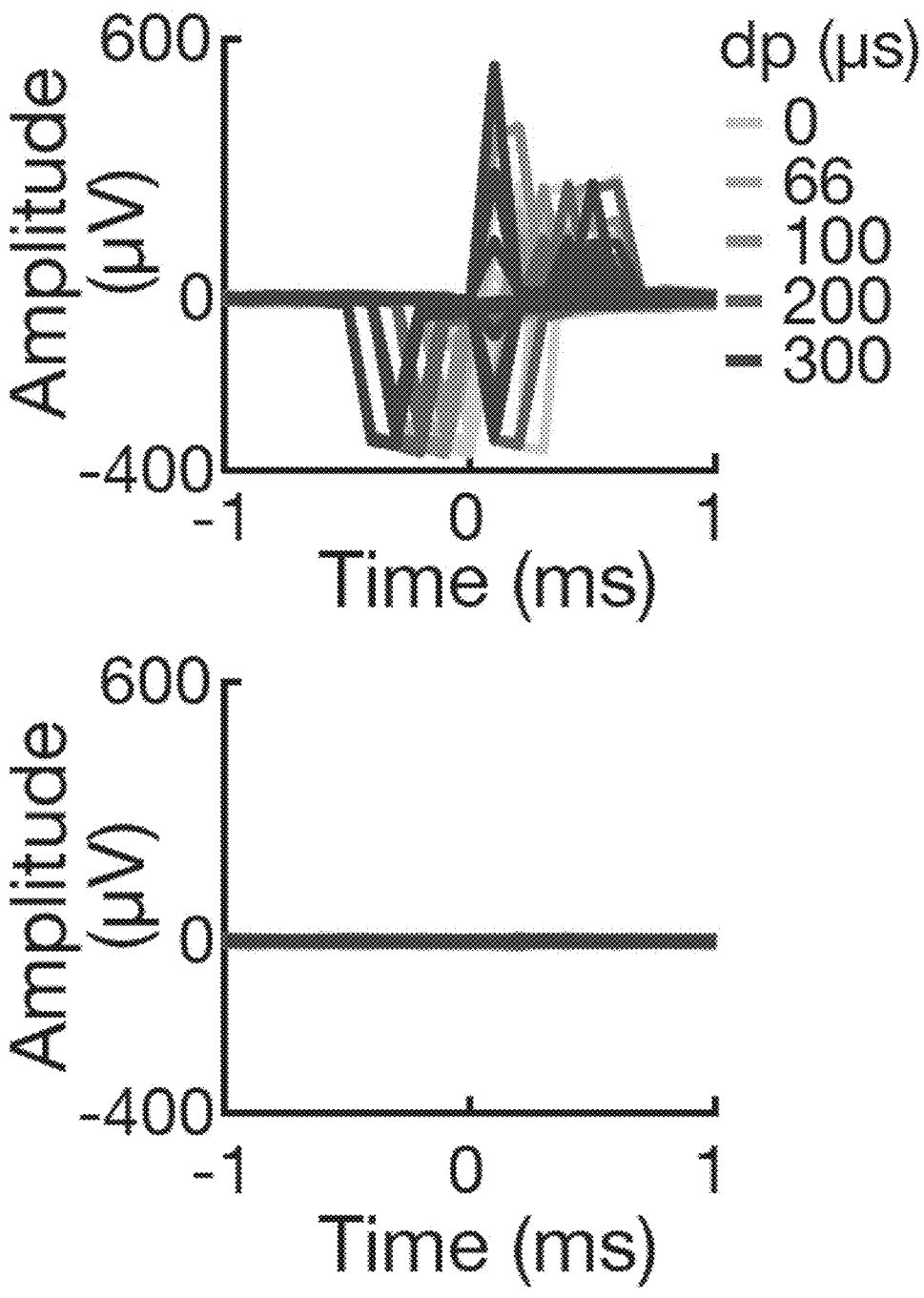
FIG. 11C (C) contains graphs summarizing the averaged (n=60) amplitudes of the saline artifacts for each pulse shape prior to (top) and after (bottom) applying MPARRM.
Figure 11E:
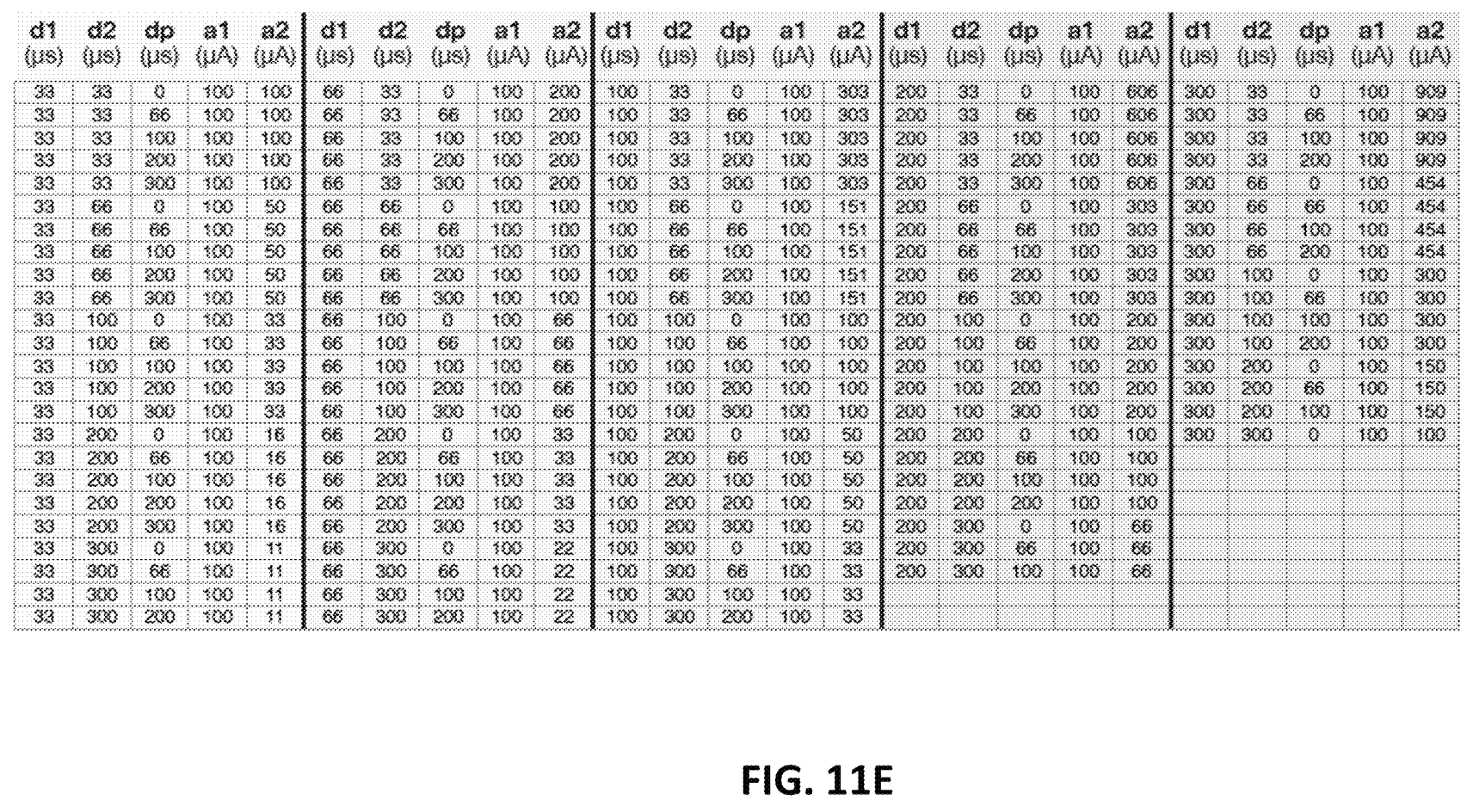

We further applied the MPARRM directly to the saline stimulation signal. FIG. 11C (top) shows the original signal indicating different pulse shapes. FIG. 11C (bottom) shows the averaged amplitude decreased from 34.1 pV to 2.5 pV after applying MPARRM. FIG. 11D2 further confirms that MPARRM could remove the artifact for different pulse shapes and different sampling rates. Quantitative comparison with raw signal. To verify the artifact removal performance, we compared the clean signals (after applying MPARRM or interpolate denoising method) with the raw signals over time. We extracted the bin (5 ms) mean value (step by 2 ms from 0 to 50 ms following artifact onset) of the power signals of each trial and performed three different measurements (i.e., correlation, sensitivity, specificity).

We performed the analysis for each frequency band and pulse shape separately. We calculated the Pearson correlation R between the bin mean band power value of the raw signal and clean signal for each bin step. Next, we calculated the average R along each bin step (mean±s.d.; n=49500 for MPARRM across all pulse shapes and electrodes, red; n=450 for interpolate denoising method across all electrodes, blue; FIG. 9B, left). The averaged R for the signal frequency ranges ($\theta$, $\alpha$, l$\beta$, h$\beta$, l$\gamma$, b$\gamma$) at 5 ms after SPES onset was (1, 1, 1, 1, 1, 0.98) and (1, 1, 1, 0.99, 0.92, 0.46) for MPARRM and interpolate denoising, respectively. Both methods showed good performance in low frequencies. However, MPARRM showed a better performance in higher frequencies, especially for broadband gamma (0.98 vs. 0.46). The performance of MPARRM and interpolate denoising tended to merge together after the stimulation onset at time=0 (FIG. 9B, left).

Since we added the saline SPES artifact around 300 ms after auditory stimulus onsets, we could expect a strong power modulation by auditory stimulus around the saline SPES onset (FIG. 9A2). To quantify the modulation effect of the denoising methods, we performed a one-sample t-test of the bin mean band power value for each bin step of each electrode (the power signals were z-scored with the baseline). Electrode measurements with p<0.01 (two-tailed) were significantly modulated by an auditory stimulus.

We calculated the sensitivity (FIG. 9B, middle) and specificity (FIG. 9B, right) of the clean signal to faithfully reveal the auditory modulation in the raw signal in each frequency band. Sensitivity and specificity were determined using the relation Sensitivity=TP/(TP+FN), and Specificity=TN/(TP+FN) as defined TP, TN, FP, and FN are defined in TABLE 1 below.

TABLE 3

| DEFINITIONS OF STANDARD AND TEST | | | |
|---|---|---|---|
| | | Standard | |
| | | Yes | No |
| Test | Yes | TP (true positive) | FP (False positive) |
| | No | FN (false negative) | TN (true negative) |

For purposes of evaluation using TABLE 3 criteria, for the denoised data, "standard" referred to significant auditory modulation in raw signal and "test" referred to significant auditory modulation in clean signal with MPARRM or interpolate denoising.

We calculated the average sensitivity and specificity along each bin step across all pulse shapes for MPARRM (mean±s.d., n=110). Both denoising methods had similar and high sensitivity and specificity for low frequencies at 5 ms after SPES onset. However, MPARRM shows better performance for higher frequencies, especially for broadband gamma (specificity equal to 99% and 23% for MPARRM and interpolate denoising, respectively). The performance of MPARRM and interpolate denoising tended to merge together after the stimulation onset (FIG. 9B, middle and left).

Early responses after applying the denoising methods. We were especially interested in the early broadband gamma response, which has been shown to be tightly correlated with multi-unit spiking activity. We calculated the averaged early response of broadband gamma (by) (i.e., 5 ms to 10 ms following the SPES onset). Topographical distribution of FIG. 9C1 showed the z-scored broadband gamma power of raw signal (left), clean signal applying MPARRM (right), and clean signal applying interpolate denoising (middle). The MPARRM shows a perfect performance with a high correlation (R=0.99, Pearson, FIG. 9C2, bottom), while the interpolate denoising failed to accurately reproduce the activation distribution (R=0.31, Pearson, FIG. 9C2. top).

Figure 9D:
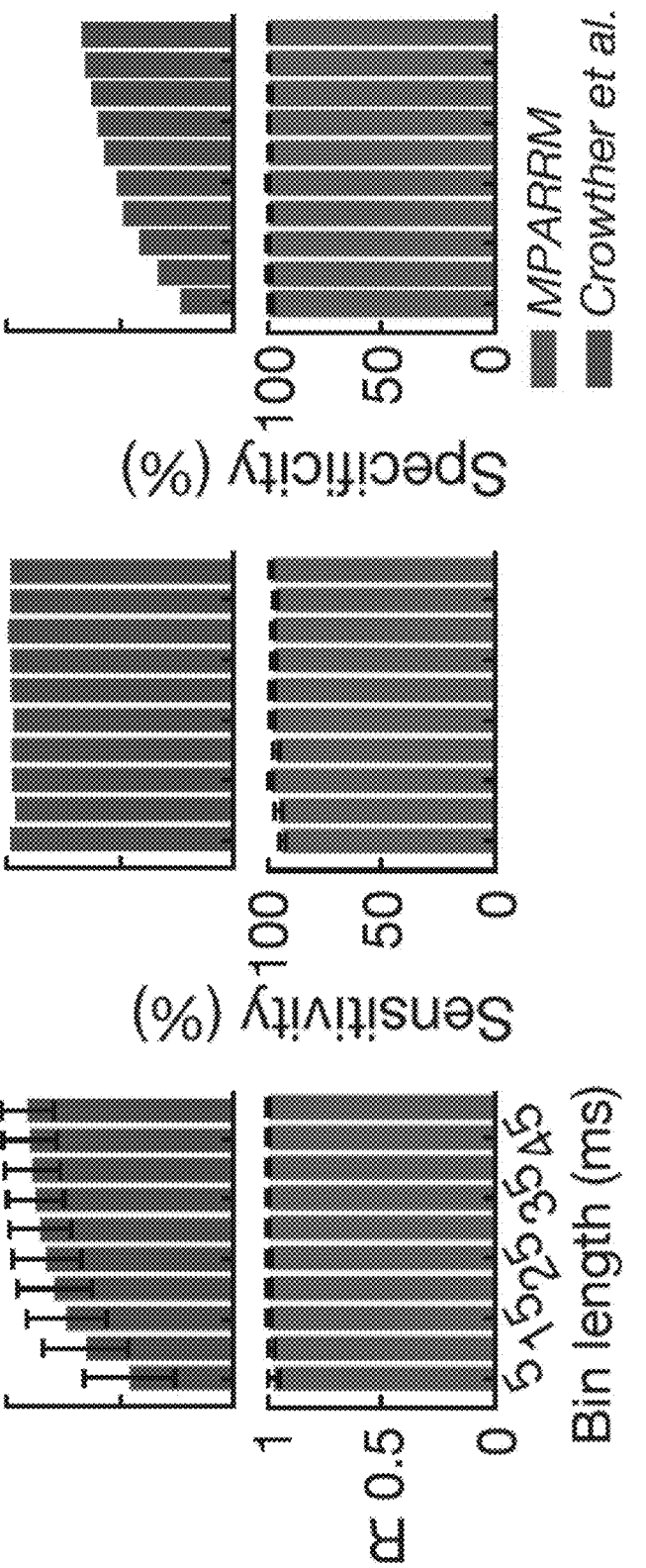
FIG. 9D contains bar graphs of the correlation between the raw signal and clean signal within various frequency bands using MPARRM (left), sensitivity (middle), and specificity (right) using MPARRM (red) and interpolate (blue) denoising methods as a function of time bin length; increased bin length enhanced the performance of the MPARRM denoising method.

We further increased the performance by using a longer bin length. For this purpose, we selected bins with various lengths (i.e., 5, 10, . . . , 50 ms) with each bin starting at 5 ms after SPES onset. FIG. 9D shows the results of by R, sensitivity, and specificity, with increased performance as bin length increased for all measures. Specifically for MPARRM with 50 ms bin length, the average R between the clean by and raw by is 0.998 (mean±s.d._n=49500), and the averaged sensitivity and specificity are 98.2% and 99.6%.

Figures 10C, 10D:
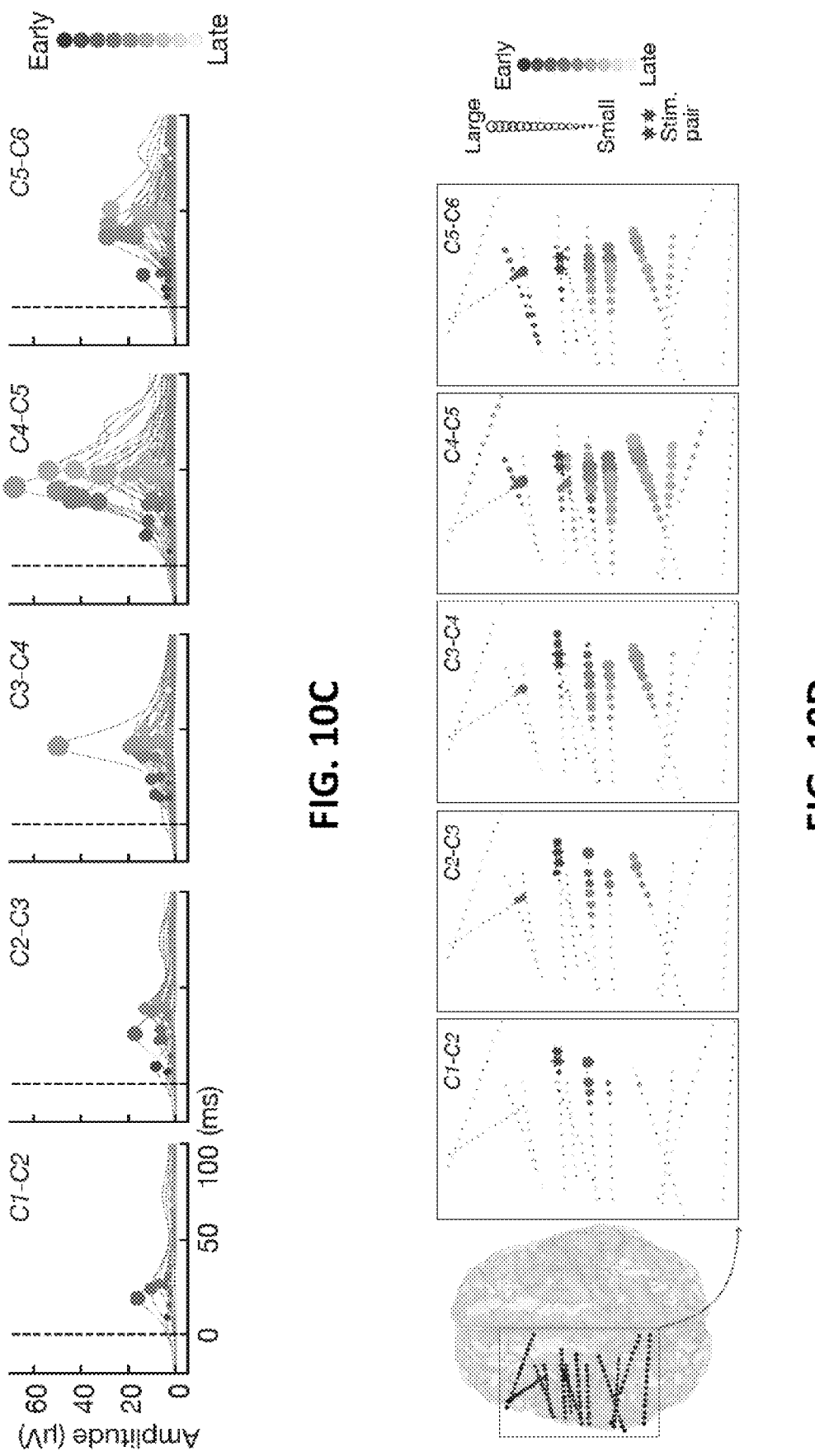
FIG. 10C is a series of graphs summarizing the trial averaged broadband gammas with MPARRM (grey lines) for each electrode and each of the five stimulation pairs described in FIG. 10B. The colored dots denote peaks within 5 ms to 50 ms after SPES onset.
FIG. 10D is a series of graphs showing the spatial distribution of broadband gamma response with MPARRM for each stimulation pair described in FIG. 10B; spatial distributions are presented within the red box overlaid on the brain image shown on the far left.

Verifying the denoising methods with human SPES signals. We further verified the denoising methods on the human SPES signals. FIG. 10A shows raw signal traces and clear signal traces (applying MPARRM) of one representative electrode. The stimulation artifacts around time 0 had vanished. FIG. 10B shows the averaged broadband gamma response with MPARRM (left) and interpolate denoising (right) for different stimulation pairs along amygdala and hippocampus. There was a strong residual artifact around time 0 with the interpolate denoising method. We further detected the peaks of broadband gamma response within 5 ms to 50 ms (FIG. 10C), which allowed us to track the spatial neural response from a very early time (around 5 ms), as summarized in FIG. 10D.

What is claimed is:

1. A system for removing brain stimulation artifacts in electrophysiological signals, the system comprising at least one processor and a non-transitory computer-readable media (CRM) storing a plurality of executable instructions which, when executed using the at least one processor, cause the system to:

a. decompose, by matching pursuit, a raw signal trace into a plurality of line noise atoms representative of line noise, the raw signal trace comprising a time history of the electrophysiological signals as measured;

b. subtract a summation of the plurality of line noise atoms from the raw signal trace to produce a de-noised trace;

c. identify a stimulation time window containing a portion of the denoised trace containing a brain stimulation event and replacing a portion of the denoised trace within the stimulation window with a line connecting pre-stimulation window and post-stimulation window portions of the denoised trace to produce a stimulation-free trace;

d. decompose by matching pursuit the stimulation-free trace into a plurality of evoked potential atoms representative of an evoked potential;

e. subtract a summation of the plurality of evoked potential atoms from the de-noised trace to produce an evoked potential-free trace;

f. decompose by matching pursuit, the evoked potential-free trace into a plurality of stimulation artifact atoms representative of a stimulation artifact; and g. subtract a summation of the plurality of stimulation artifact atoms from the evoked potential-free trace to produce an artifact-free trace.

2. The system of claim 1, wherein the plurality of line noise atoms, the plurality of evoked potential atoms, and the plurality of stimulation artifact atoms are selected from a stored library of atoms.

3. The system of claim 2, wherein the stored library comprises a plurality of atoms comprising Gabor atoms, Dirac atoms, sharp Gaussian atoms, and Fourier atoms.

4. The system of claim 1, wherein the line noise atoms comprise atoms characterized by atom frequencies greater than 55 Hz that extend over a full duration of the raw signal trace.

5. The system of claim 1, wherein the evoked potential atoms comprise atoms characterized by atom frequencies less than 70 Hz that extend over a full duration of the raw signal trace.

6. The system of claim 1, wherein the stimulation artifact atoms comprise atoms characterized by atom frequencies greater than 70 Hz or Dirac atoms that are centered around an onset of the brain stimulation event and extend over less than the full extent of the raw signal trace.

7. The system of claim 1, wherein the stimulation time window extends from about 5 ms prior to the brain stimulation event to about 5 ms after the brain stimulation event.

8. The system of claim 1, wherein the further comprising receiving, at the computing device, the raw signal trace.

9. The system of claim 1, further comprising isolating a portion of the raw signal trace, the portion comprising signals within a biologically relevant frequency band selected from theta comprising from 4 to 7 Hz, alpha comprising from 8 to 12 Hz, low beta comprising from 13 to 20 Hz, high beta comprising from 20-30 Hz, low gamma comprising from 30-50 Hz, broadband gamma from 70-170 Hz, and any combination thereof.

10. The system of claim 1, wherein the brain stimulation event comprises a single pulse electrical signal.

\* \* \* \* \*